(12) United States Patent
Detamore et al.

(10) Patent No.: US 8,669,107 B2
(45) Date of Patent: Mar. 11, 2014

(54) METHOD OF PREPARING A TISSUE ENGINEERING SCAFFOLD COMPRISING A PLURALITY OF MICROSPHERES LINKED TOGETHER

(75) Inventors: Michael Detamore, Lawrence, KS (US); Milind Singh, Lawrence, KS (US); Aaron M. Scurto, Oskaloosa, KS (US); Cory Berkland, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 13/591,087

(22) Filed: Aug. 21, 2012

(65) Prior Publication Data

US 2012/0313284 A1 Dec. 13, 2012

Related U.S. Application Data

(62) Division of application No. 12/248,530, filed on Oct. 9, 2008, now Pat. No. 8,277,832.

(60) Provisional application No. 60/978,831, filed on Oct. 10, 2007.

(51) Int. Cl.
*C12N 5/00* (2006.01)
*C12N 5/07* (2010.01)
*C12N 11/08* (2006.01)
*A61F 2/00* (2006.01)

(52) U.S. Cl.
USPC ........... 435/395; 424/423; 424/93.7; 435/180

(58) Field of Classification Search
None
See application file for complete search history.

(56) References Cited

U.S. PATENT DOCUMENTS 5,866,155 A * 2/1999 Laurencin et al. ............. 424/425
6,281,256 B1 * 8/2001 Harris et al. .................... 521/51
7,731,756 B2 * 6/2010 Maspero et al. ........... 623/23.51

OTHER PUBLICATIONS

Singh et al., Microsphere-Based Seamless Gradient Scaffolds for Tissue Engineering, Journal of Biomedical Materials Research, Part A, 2007, pp. 1-27, ScolarOne Manuscript Central, John Wiley & Sons, Inc.*

* cited by examiner

*Primary Examiner* — David M Naff
(74) *Attorney, Agent, or Firm* — Maschoff Brennan, PLLC

(57) ABSTRACT

Methods can prepare tissue engineering scaffolds that include a plurality of biocompatible microspheres linked together to form a three-dimensional matrix. The matrix can include a plurality of pores for growing cells. The biocompatible microspheres can include first and second sets of microspheres. The first set of microspheres can have a first characteristic, and a first predetermined spatial distribution with respect to the three-dimensional matrix. The second set of microspheres can have a second characteristic that is different from the first characteristic, and a second predetermined spatial distribution that is different from the first predetermined spatial distribution with respect to the three-dimensional matrix. The first and second characteristics can selected a composition, polymer, particle size, particle size distribution, type of bioactive agent, type of bioactive agent combination, bioactive agent concentration, amount of bioactive agent, rate of bioactive agent release, mechanical strength, flexibility, rigidity, color, radiotranslucency, radiopaqueness, or the like.

23 Claims, 28 Drawing Sheets

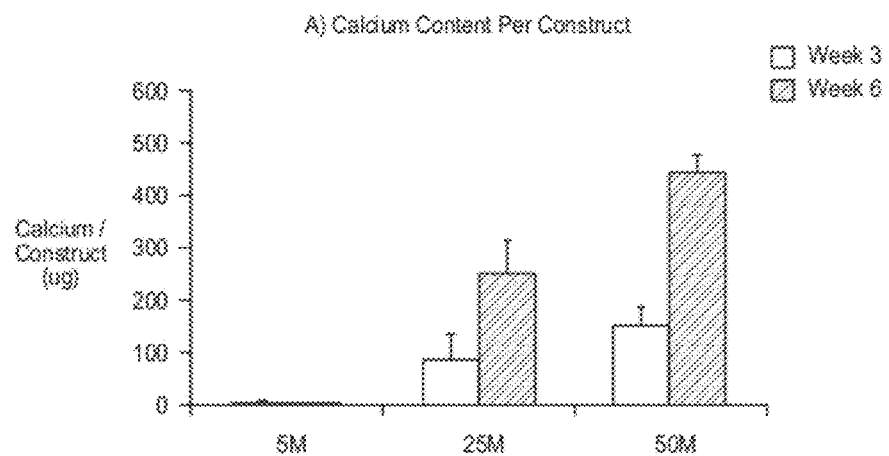
*Fig. 18*
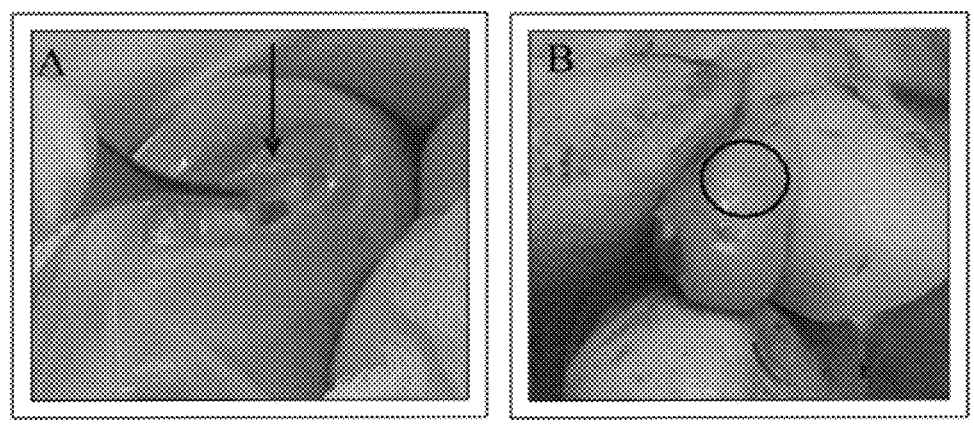
*Fig. 19A*  *Fig. 19B*

METHOD OF PREPARING A TISSUE ENGINEERING SCAFFOLD COMPRISING A PLURALITY OF MICROSPHERES LINKED TOGETHER

CROSS-REFERENCE

This patent application is a divisional application of U.S. patent application Ser. No. 12/248,530, filed Oct. 9, 2008, now U.S. Pat. No. 8,277,832, which claims benefit of U.S. Patent Application Ser. No. 60/978,831, filed Oct. 10, 2007, which provisional application is incorporated herein by specific reference in its entirety.

BACKGROUND

Spatial patterning of biological cues is of special interest to investigators in areas such as nerve tissue engineering, study of chemotaxis, etc., where gradients of surface-immobilized or soluble signaling molecules have been employed. To modulate the immune and/or inflammatory systems, controlled spatial and temporal release of anti-inflammatories or chemokines are desired. In addition, interfacial tissue engineering is another area that may benefit from scaffolds with biphasic and gradient distributions of another area that may benefit from scaffolds with biphasic and gradient distributions of bioactive signals. Previous diffusion- and convection-driven approaches for the generation of linear or non-linear signal gradients are simple and inexpensive, however restricted to the generation of limited set of profiles. Use of photolithographic and soft lithographic techniques (e.g., microcontact printing and microfluidics) can provide micron-level positional accuracy; however, such techniques are expensive and largely limited to two-dimensional constructs. Commercially available gravity- and motor-driven gradient makers (Gradient maker, CBS Scientific, CA; Gradient former, Jule, Inc., CT), designed for applications in electrophoresis, have been utilized in some tissue engineering studies (Shoichet group, West group), but can only create certain gradient profiles, and have only been used to fabricate gel-based scaffolds. In addition, although some of the previous techniques have been used to create three-dimensional scaffolds with spatial gradients of bioactive agents (e.g., soluble growth factor), little attention has been paid towards the controlled temporal release aspect.

Therefore it would be advantageous to have a three-dimensional scaffold for use as an endoprosthesis that can provide controlled spatial and temporal release of a suitable bioactive agent.

SUMMARY

The present invention includes three-dimensional tissue engineering scaffolds that can be used as endoprostheses. More particularly, the present invention relates to three-dimensional tissue engineering scaffolds that are prepared from microspheres having different characteristics.

In one embodiment, a tissue engineering scaffold for growing cells can include a plurality of biocompatible microspheres linked together so as to form a three-dimensional matrix. The matrix can include a plurality of pores defined by and disposed between the microspheres. Also, the microspheres can have a surface area sufficient for growing cells within the plurality of pores. The biocompatible microspheres can include first and second sets of microspheres. The first set of microspheres can have a first characteristic, and can have a first predetermined spatial distribution with respect to the three-dimensional matrix. The second set of microspheres can have a second characteristic that is different from the first characteristic, and can have a second predetermined spatial distribution that is different from the first predetermined spatial distribution with respect to the three-dimensional matrix. For example, the first and second characteristics can be independently selected from the group consisting of the following: composition; polymer; particle size; particle size distribution; type of bioactive agent; type of bioactive agent combination; bioactive agent concentration; amount of bioactive agent; rate of bioactive agent release; mechanical strength; flexibility; rigidity; color; radiotranslucency; radiopaqueness; or the like.

In one embodiment, the first predetermined spatial distribution of the microspheres can be distinct from and adjacent to the second predetermined spatial distribution of the microspheres. Also, the first predetermined spatial distribution of microspheres can form a first concentration gradient of the first set of microspheres, and the second predetermined spatial distribution of the microspheres can form a second concentration gradient of the second set of microspheres. Additionally, the first predetermined spatial distribution gradient and second predetermined spatial distribution gradient can blend into each other.

In one embodiment, the three dimensional matrix can include a first portion and a second portion. The first portion can have a majority of microspheres of the first set. The second portion can have a majority of microspheres of the second set. Optionally, a third portion of the three dimensional matrix can be disposed between the first portion and the second portion. The first predetermined spatial distribution in the third portion forms a first concentration gradient of the first set of microspheres and the second predetermined spatial distribution in the third portion forms a second concentration gradient of the second set of microspheres. Optionally, the first or second concentration gradient can be linear or nonlinear.

In one embodiment, the scaffold can include a first bioactive agent contained in or disposed on the first set of microspheres. The scaffold can be configured to release the first bioactive agent so as to create a first desired spatial and temporal concentration gradient of the first bioactive agent. Optionally, the second set of microspheres can be substantially devoid of the first bioactive agent, or can include a second bioactive agent. When the second bioactive agent is contained in or disposed on the second set of microspheres, the scaffold can be configured to release the second bioactive agent so as to create a second desired spatial and/or temporal concentration gradient of the second bioactive agent that is different from the first desired spatial and/or temporal concentration gradient of the first bioactive agent.

In one embodiment, the microspheres can be melded together by a portion of each microsphere merging with a portion of at least one adjacent microsphere. Methods of melding microspheres together are described herein. For example, a solvent, such as ethanol, can be used for melding.

In one embodiment, the bioactive agent contained in a microsphere can be a growth factor for growing the cells. However, the microspheres can include any type of bioactive agent. Accordingly, the first characteristic can be a first bioactive agent contained in or disposed on the microspheres, and the second characteristic can be a second bioactive agent contained in or disposed on the microspheres. For example, the first bioactive agent can be an osteogenic factor and the second bioactive agent can be a chondrogenic factor.

In one embodiment, at least one of the first set or second set of microspheres can include a biodegradable polymer. For example, the microspheres can include a poly-lactide-co-glycolide or poly(lactic-co-glycolic acid).

In one embodiment, the scaffold can include a medium sufficient for growing cells disposed in the pores. The medium can be a cell culture media. Additionally, the medium can be a body fluid or tissue.

In one embodiment, the scaffold can include a plurality of cells attached to the plurality of microspheres and growing within the pores. Such cells can include a first cell type associated with the first set of microspheres, and a second cell type associated with the second set of microspheres.

In one embodiment, the scaffold can include a third set of microspheres having a third characteristic that is the same or different from the first or second characteristics. The third set of microspheres can have a third predetermined spatial location that is different from the first or second predetermined spatial locations with respect to the three-dimensional matrix.

In one embodiment, the scaffold can include a first end and an opposite second end. Accordingly, the first set of microspheres can have a first bioactive agent, and the first end can have a majority of microspheres of the first set. Correspondingly, the second set of microspheres can have a second bioactive agent that is different from the first bioactive agent, and the second end having a majority of microspheres of the second set.

In one embodiment, the present invention can include a method of preparing tissue engineering scaffold for growing cells. Such a method can include the following: providing a first set of microspheres having a first characteristic; providing a second set of microspheres having a second characteristic that is different from the first characteristic; and linking the microspheres of the first set and second set together so as to form a three-dimensional matrix having a plurality of pores defined by and disposed between the microspheres. The plurality of microspheres can have a surface area sufficient for growing cells within the plurality of pores. The three-dimensional matrix can include a first set of microspheres having a first predetermined spatial distribution with respect to the three-dimensional matrix, and a second set of microspheres having a second predetermined spatial distribution that is different from the first predetermined spatial distribution with respect to the three-dimensional matrix.

In one embodiment, the process of linking the microspheres together can include melding the microspheres such that the microspheres are melded together by a portion of each microsphere merging with a portion of at least one adjacent microsphere.

In one embodiment, the method of preparing a microsphere-based scaffold can include any one of the following: preparing a first liquid suspension of the first set of microspheres; preparing a second liquid suspension of the second set of microspheres; introducing the first liquid suspension into a mold; introducing the second liquid suspension into the mold before, during, and/or after introducing the first liquid suspension into the mold; introducing a solvent into the mold such that the solvent melds the microspheres of the first set and second set together into the three-dimensional matrix; and/or removing the solvent from the melded microspheres.

In one embodiment, the present invention can include a method of generating or regenerating tissue in an animal, such as a human. The method can include providing an endoprosthesis for growing cells. The endoprosthesis can have a plurality of biocompatible microspheres linked together so as to form a three-dimensional matrix having a plurality of pores defined by and disposed between the microspheres. Accordingly, the endoprosthesis can include a microsphere-based scaffold. The plurality of microspheres can have a surface area sufficient for growing cells within the plurality of pores. The biocompatible microspheres can be characterized as described herein. Additionally, the method of generating or regenerating tissue can include implanting the endoprosthesis in the animal such that cells grow on the microspheres and within the pores. This process can be used to grow specific types of cells for growth of tissue, bone, cartilage, or the like.

In one embodiment, the method of generating or regenerating tissue can include any one of the following: introducing a cell culture media into the pores; introducing cells into the pores; and/or culturing the cells such that the cells attach to the microspheres and grow within the pores.

These and other embodiments and features of the present invention will become more fully apparent from the following description and appended claims, or may be learned by the practice of the invention as set forth hereinafter.

FIGURES

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 5A shows live cells, FIG. 5B shows dead cells, and FIG. 5C is a combination of FIGS. 5A-5B.

FIG. 9A) collagen I, FIG. 9B) collagen II, and FIG. 9C) is a negative control.

Figure 15:
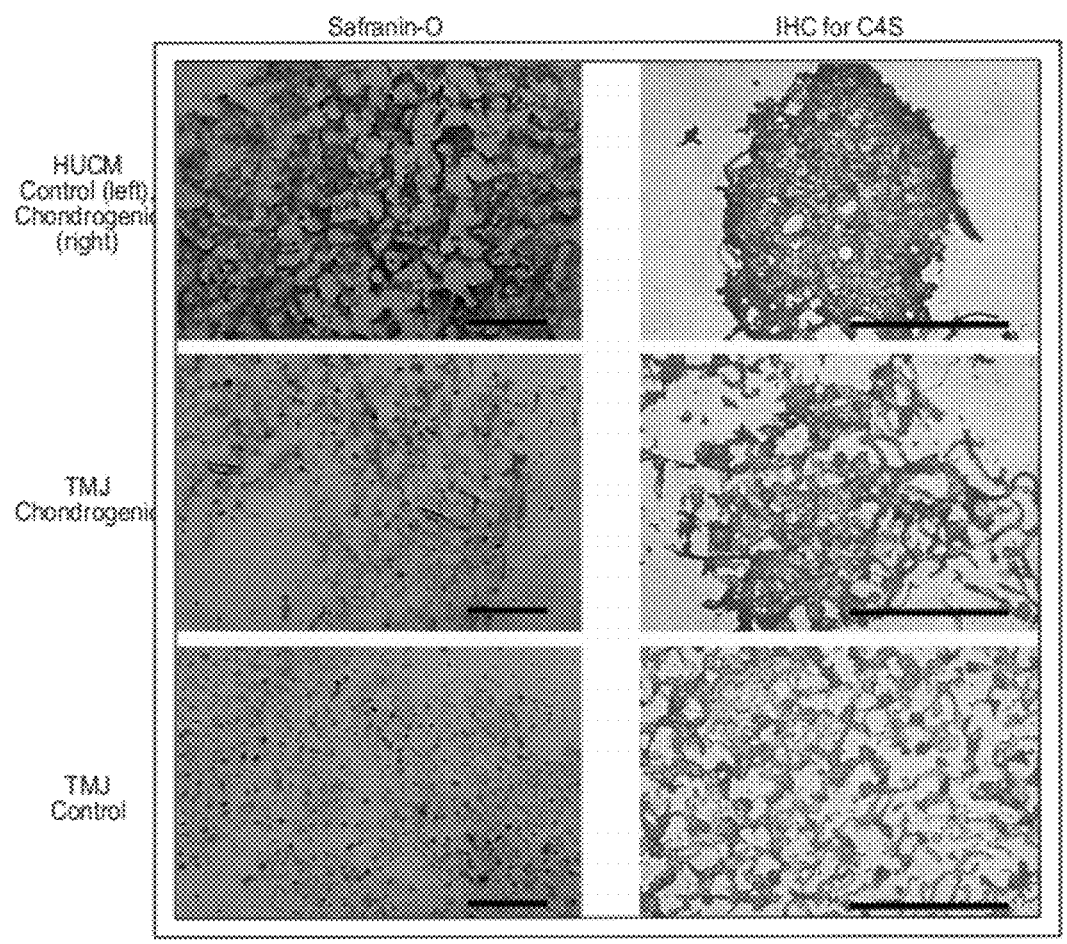

FIG. 15 includes histological photographs of hUCMSCs grown in nonwoven poly-glycolic acid (PGA) scaffolds.

Figure 16:
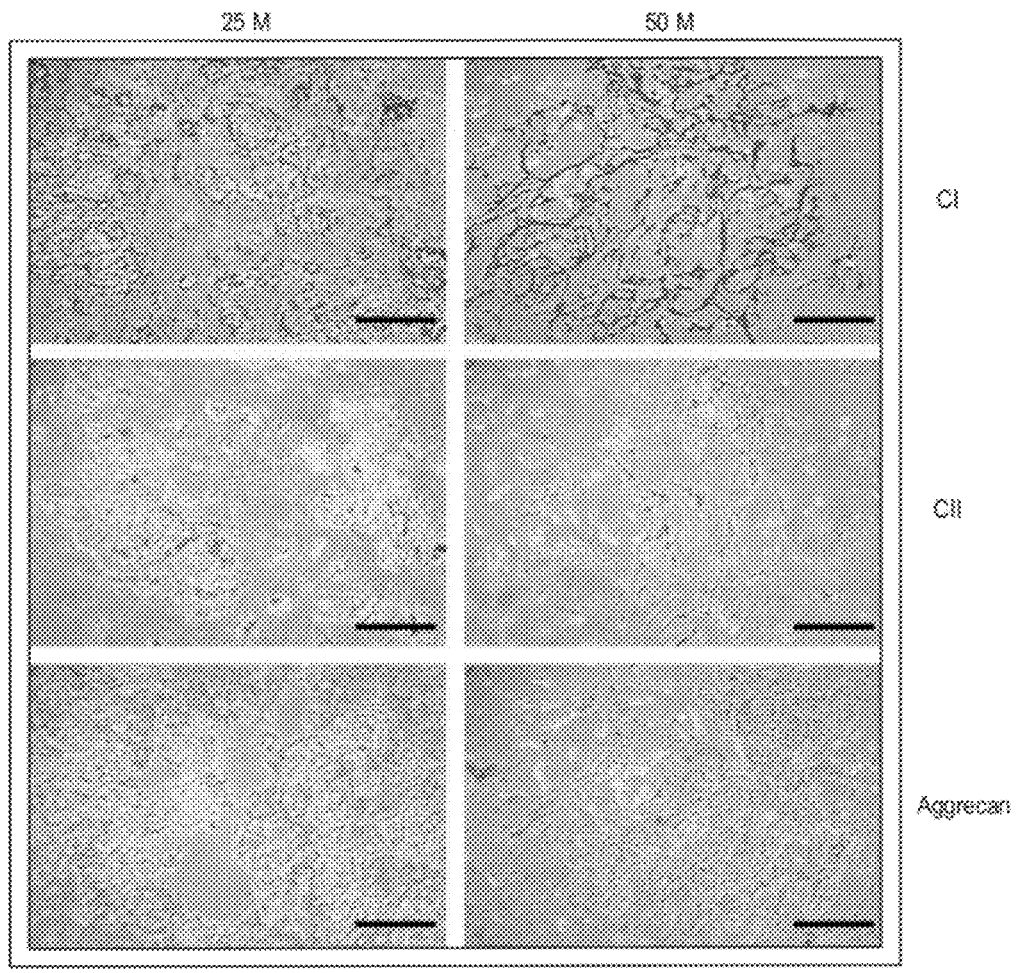

FIG. 16 includes histological photographs of IHC staining for collagen types I and II and aggrecan hUCMSCs grown in nonwoven poly-glycolic acid (PGA) scaffolds.

Figure 17A:
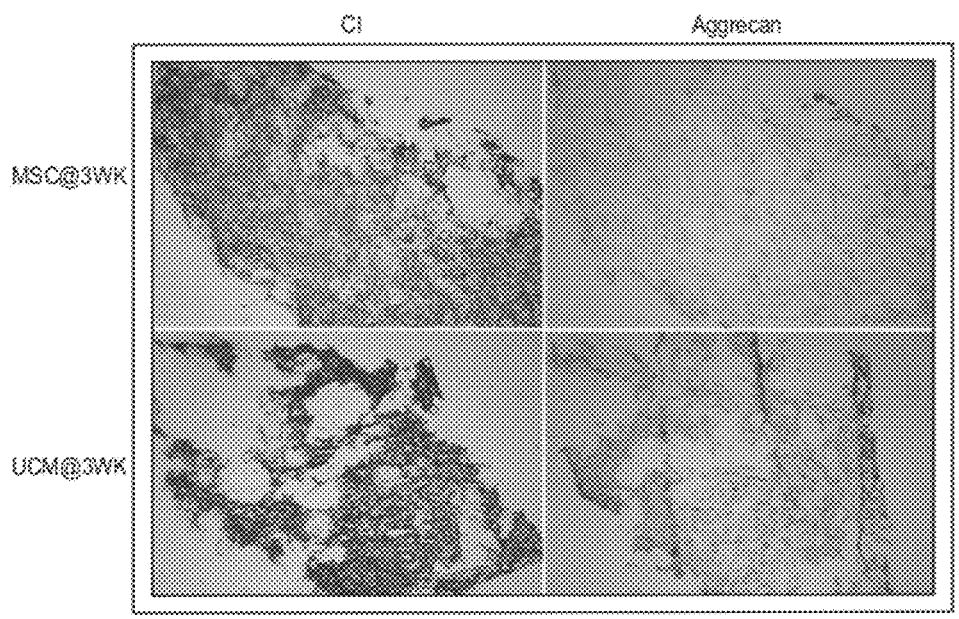

FIG. 17A includes histological photographs that show immunohistochemical staining for collagen type I and aggrecan after 3 weeks of culture on PGA scaffolds.

Figure 17B:
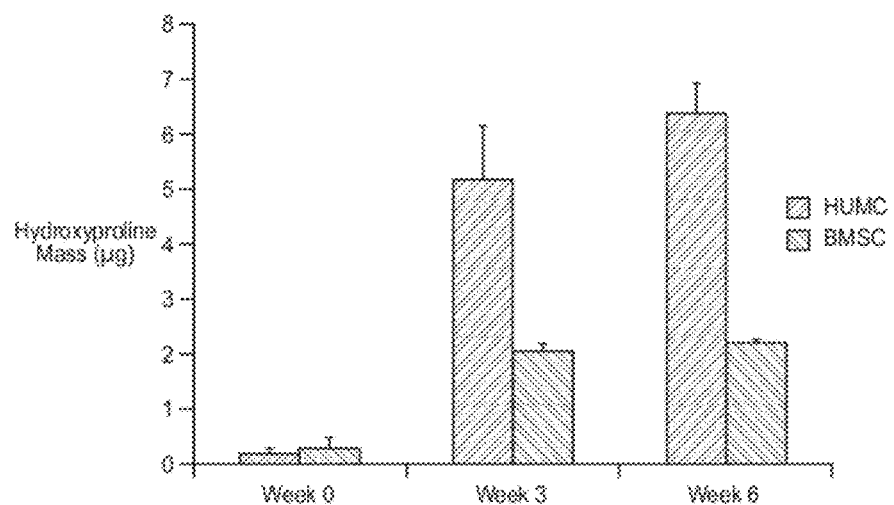

FIG. 17B shows hydroxyproline content for hUCMSC and BMSCs after 3 and 6 weeks of culture.

FIG. 18 is a graph that illustrates mineralization after in vitro culture of hUCMSCs on nonwoven poly-glycolic acid (PGA) scaffolds.

FIGS. 19A-19B are photographs that show surgical implantation of a microsphere-based scaffold and tissue growth over the microsphere-based scaffold.

Figure 20A:
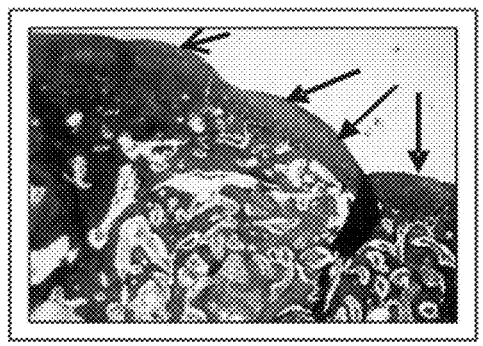
Figure 20B:
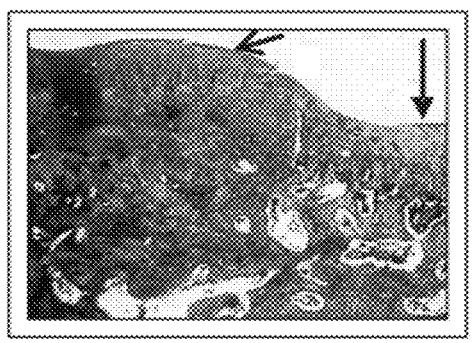

FIGS. 20A-20B show histological results following 6 weeks of microsphere-based scaffold implantation in rabbit knees, and show Saf-O/Fast green staining of the implant/tissue.

Figure 20C:
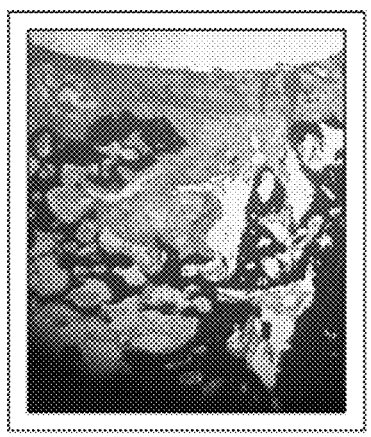

FIG. 20C includes histological photographs with Von Kossa staining.

Figure 20D:
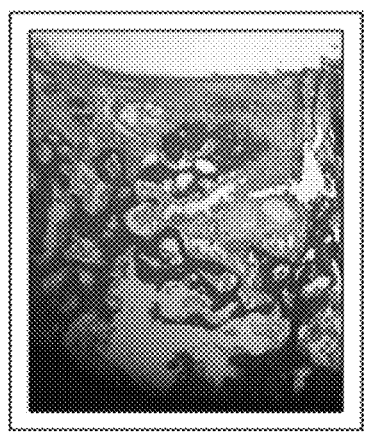

FIG. 20D includes histological photographs with Alizarin Red staining.

Figure 21:
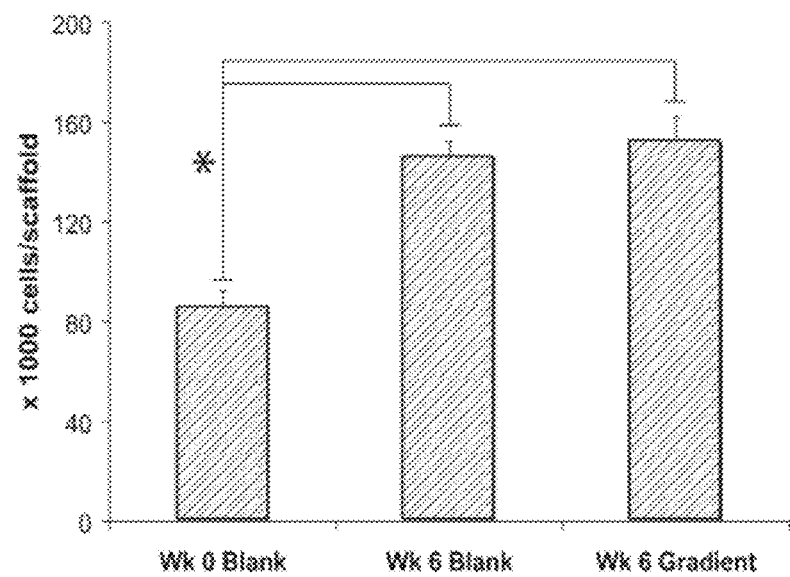

FIG. 21 is a graph that shows the growth in cell numbers on blank and gradient microsphere-based scaffolds.

Figure 22:
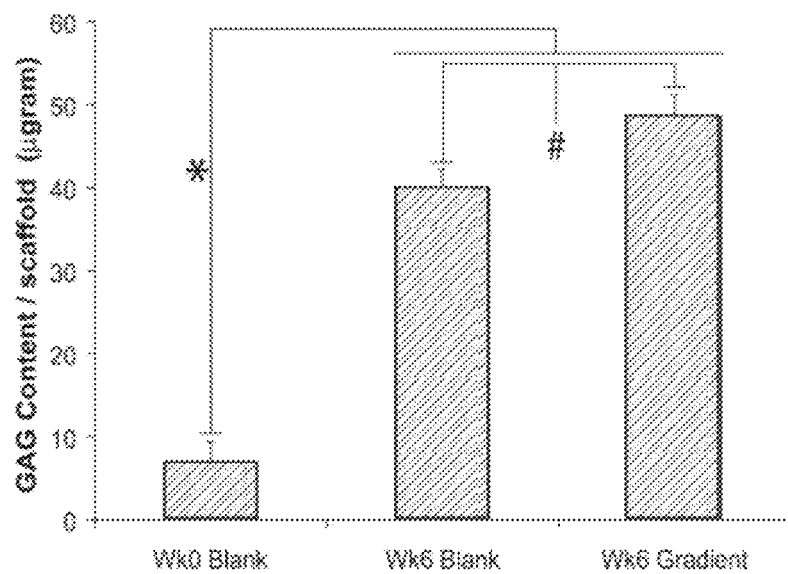

FIG. 22 is a graph that shows the glycosaminoglycan production from cell growth on blank and gradient microsphere-based scaffolds.

Figure 23A:
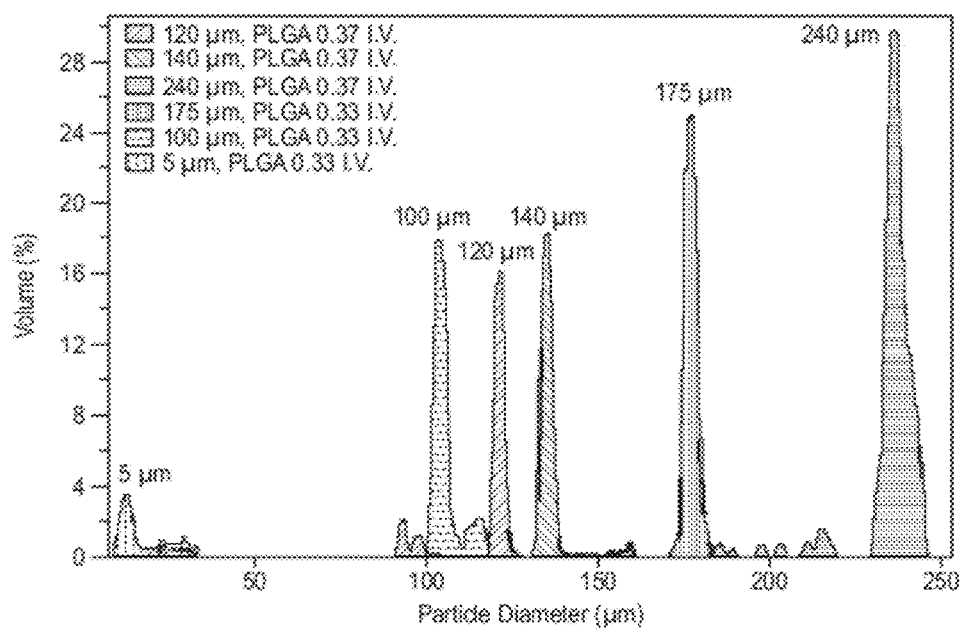

FIG. 23A is a graph of a Coulter multisizer size distribution plot of PLG microspheres of different nominal sizes, displaying the monodispersity of the microspheres with discrete peaks (e.g., peaks with % volume less than 0.5 have been omitted for the sake of clarity).

FIG. 23 B includes an image of various shape-specific scaffolds that were produced with PLG microspheres (140 μm) using CO2 at sub-critical conditions (15 bar for 1 hour at 25° C. followed by depressurization at ~0.14-0.21 bar/s) utilizing rubber molds of different shapes (e.g., From left to right: cylinder, bilayered cylinder, tube, plus-sign, and star shapes).

Figure 24A:
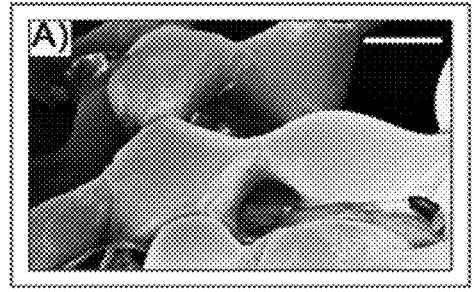
Figure 24B:
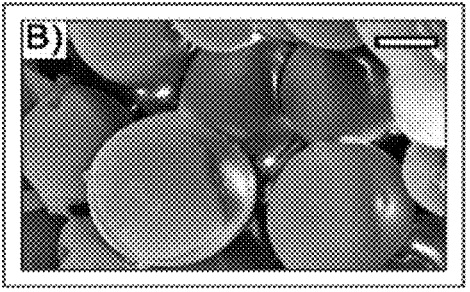
Figure 24C:
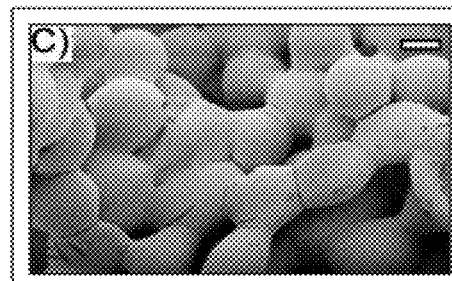
Figure 24D:
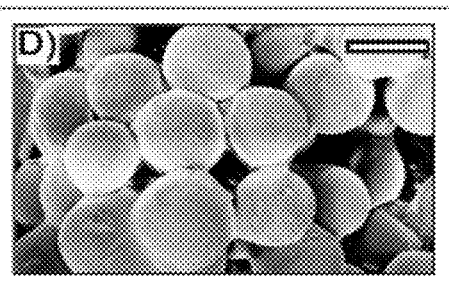
Figure 24E:
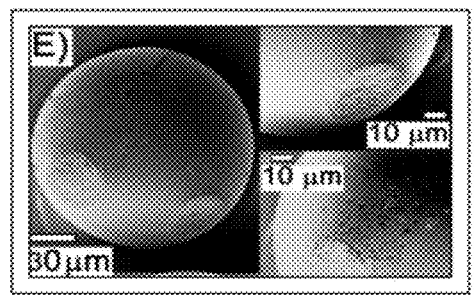
Figure 24F:
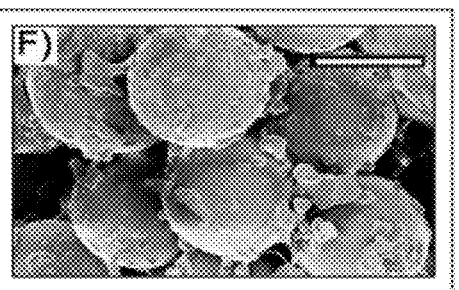

FIGS. 24A-24F include scanning electron micrographs of scaffolds fabricated using different types of PLG microspheres at processing conditions for sintering (e.g., CO2 exposure at 15 bar for 1 hour at 25° C. followed by depressurization at ~0.14-0.21 bar/s). Sizes of the microspheres used were 240 μm (FIGS. 24A-24B), 175 μm (FIG. 24C), 140 μm (FIGS. 24D-24E), and 140 μm together with 5 μm (FIG. 24F). The morphology of a microsphere following the CO2 sintering (FIG. 24E) is also displayed.

Figure 25:
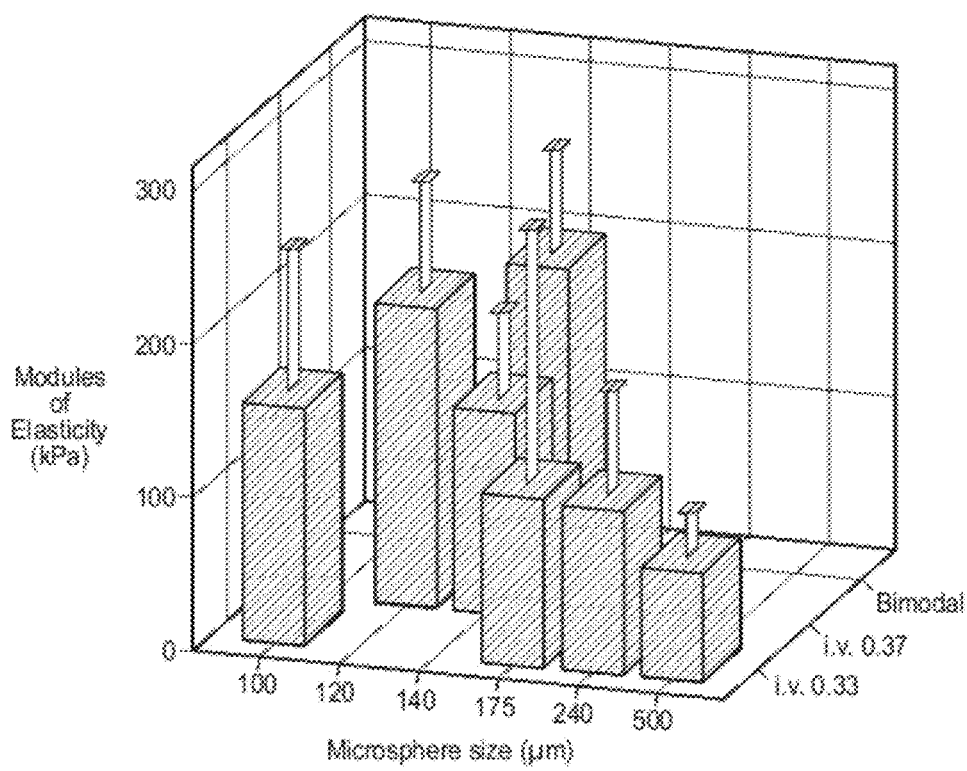

FIG. 25 is a graph of the modulus of elasticity of the scaffolds prepared using different microspheres sizes.

Figures 26A, 26B, 26C:
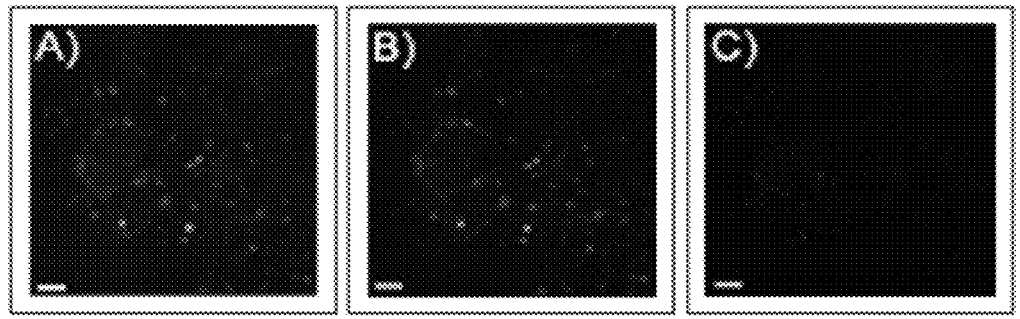

FIG. 26A-26C includes fluorescence micrographs of live/dead dye-stained porcine chondrocytes seeded on CO2-sintered microsphere-based scaffolds (175 μm) following a 3 week cell culture period: FIG. 26A) live and dead cells, FIG. 26B) live cells only, and FIG. 26C) dead cells only.

Figure 26D:
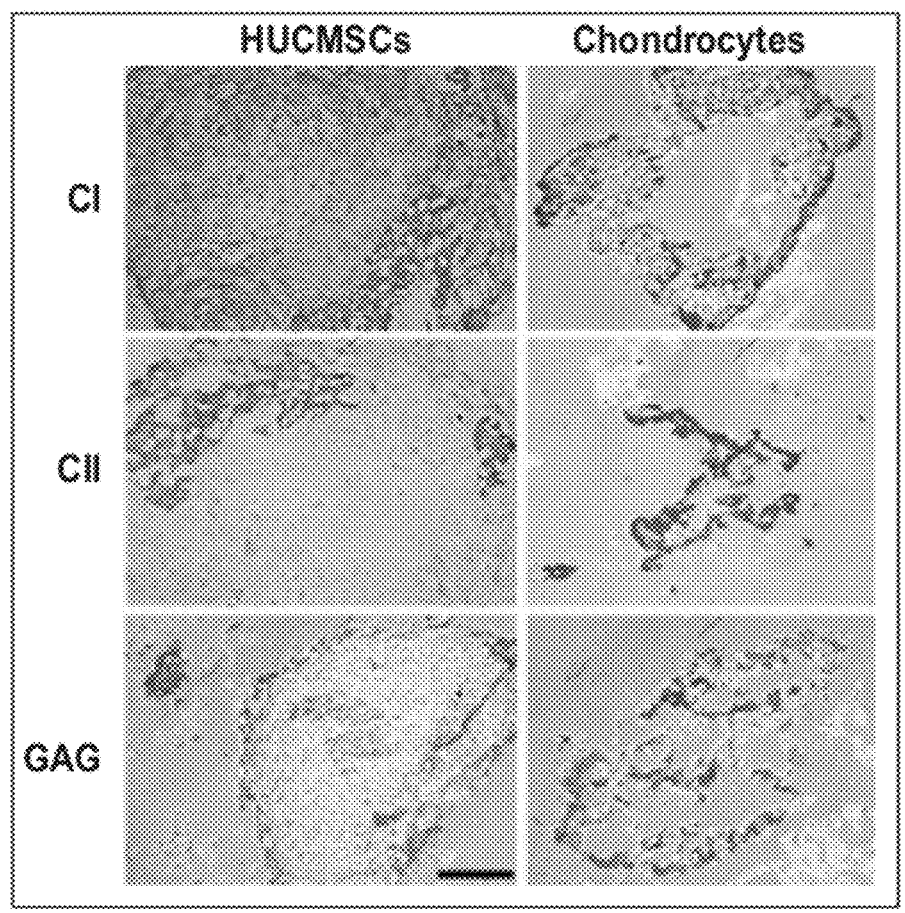

FIG. 26D includes pictures of immunohistochemistry staining for collagen types I and II after 3 weeks of culture on CO2-sintered microsphere-based scaffolds: HUCMSCs=human umbilical cord mesenchymal stromal cells, CI=collagen type I, CII=collagen type II, and GAG=glycosaminoglycan.

Figure 27A:
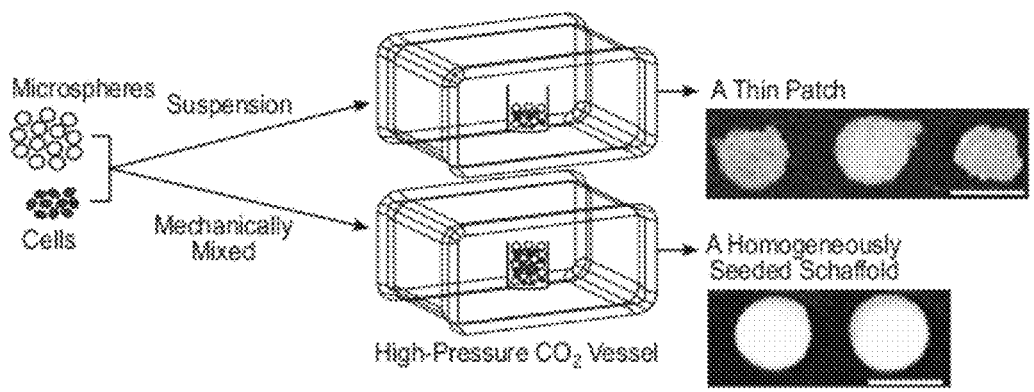

FIG. 27A is a schematic representation of a process of producing a microsphere-based cell-loaded scaffold or thin patch with gaseous CO2. The process of combining the cells and microparticles in a liquid medium results in a melded thin patch (top), whereas mechanically mixing a loose cell pellet in a minimal liquid volume with the microparticles results in a homogeneously seeded scaffold.

Figure 27B:
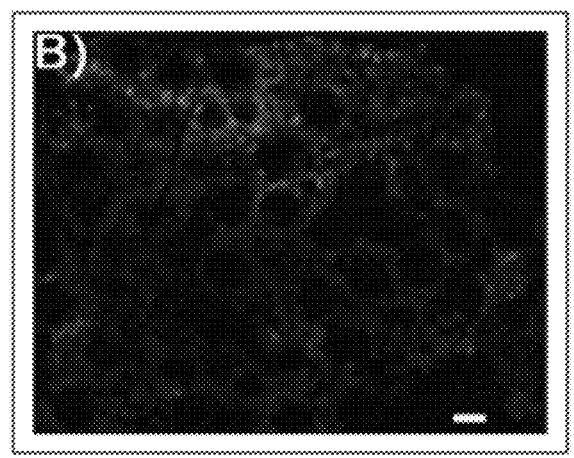
Figure 27C:
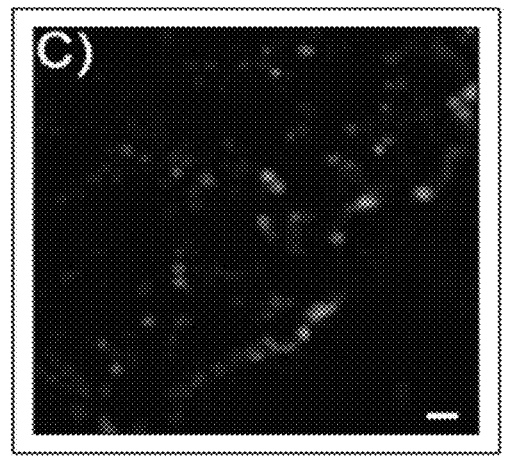

FIGS. 27B-27C include fluorescence micrographs of live/dead dye-stained hUCMSCs that display cell survival following CO2 sintering of microspheres (120 μm) at sub-critical (gaseous) conditions. FIG. 27B is a thin patch, and FIG. 27C is a macroscopic scaffold.

FIGS. 28A-28D are micrographs showing morphological characteristics of microspheres with various encapsulated nanophase materials.

Figure 29A:
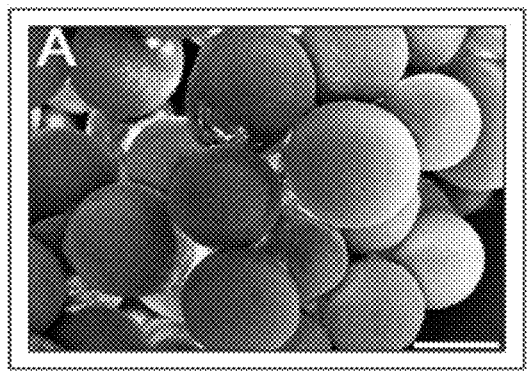
Figure 29C:
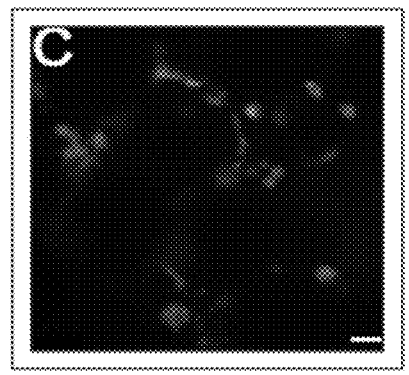
Figure 29B:
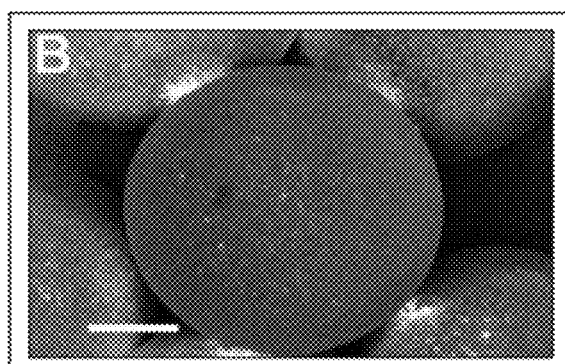

FIGS. 29A-29C include characteristic SEM micrographs of a scaffold, prepared by sintering the microspheres (90:10 PLGA:CaCO3) using ethanol sintering.

Figure 29D:
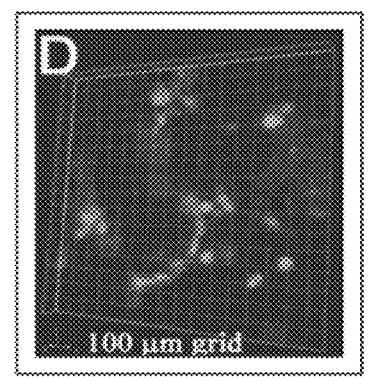
Figure 30A:
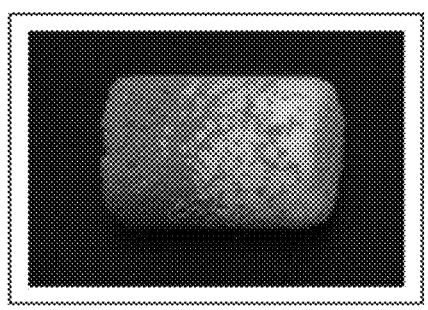

FIG. 29D is a micrograph of a 100 μm thick section of an interior section of a scaffold FIG. 30A is an image of a gradient scaffold prepared using dye (Rhodamine B)-loaded PLGA microspheres and 90:10 PLGA:CaCO3 microspheres using a 2 hour ethanol soak.

Figure 30B:
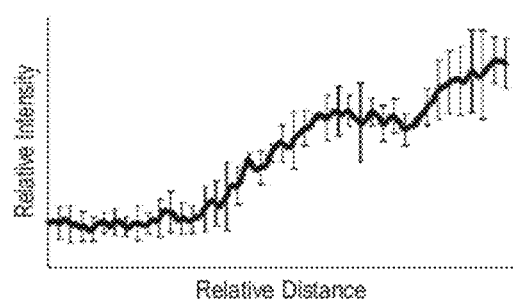

FIG. 30B is a graph that shows the fluorescent gradient which corresponds with the microsphere gradient.

Figure 31:
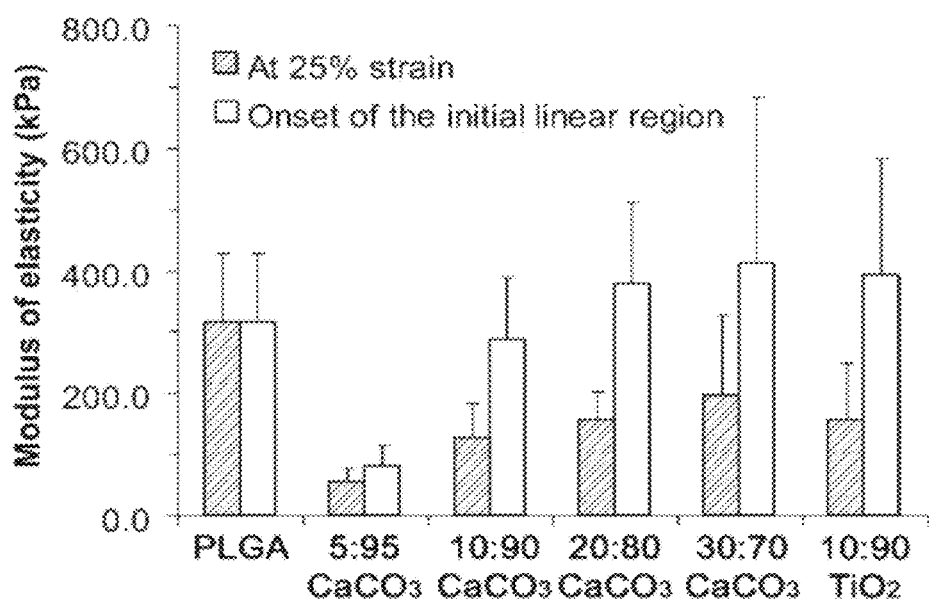

FIG. 31 is a graph that shows the moduli of elasticity of the homogeneous scaffolds prepared using different types of microspheres.

DETAILED DESCRIPTION

Spatial and temporal control of bioactive signals in three-dimensional (3-D) tissue engineering scaffolds is greatly desired. Coupled together these attributes may mimic and maintain complex biological signal patterns, such as those observed during axonal regeneration or neovascularization. Seamless polymer tissue engineering scaffolds may provide a route to achieve precise spatial control of signal distribution. A novel microparticle-based scaffold fabrication technique can provide such seamless scaffolds. A method of creating 3-D scaffolds with spatial control over model dyes using uniform Poly(D,L-lactide-co-glycolide) (PLG) microspheres can prepare such seamless scaffolds. Uniform microspheres can be produced using a Precision Particle Fabrication technique. Scaffolds can be assembled by flowing microsphere suspensions into a cylindrical glass mold, and fusing the microspheres to form a continuous, seamless scaffold using ethanol as a melding agent. Morphological and physical characterization of the scaffolds can show microsphere matrices are porous and well connected, and the compressive stiffness of the scaffolds can range from 4.2 to 6.0 MPa. Culturing chondrocytes on the scaffolds can show the compatibility of these substrates with cell attachment and viability. In addition, bi-layered, multi-layered and gradient scaffolds can be fabricated, exhibiting excellent spatial control and resolution. Such novel scaffolds can serve as sustained delivery devices of heterogeneous signals in a continuous and seamless manner, and can be particularly useful in interfacial tissue engineering.

I. Microsphere-Based Scaffolds

A novel and cost-efficient method has been developed in order to create microsphere-based three-dimensional materials with precise control over their spatial patterns/profiles of biomaterials, porosity and/or bioactive signals, which may be utilized in a variety of applications, such as tissue generation and/or regeneration. Moreover, with a suitable choice of biomaterial, it has been shown that the synthesis and encapsulation process is conducive to cell viability. Specifically, the technique can be used to create gradient scaffolds that can be used in diverse areas of tissue engineering applications, including nerve tissue engineering, study of chemotaxis, directed angiogenesis, spatial regulation of chemokines for modulating immune response, interfacial tissue engineering, and the like.

Microsphere-based three-dimensional tissue engineering scaffolds can contain predefined spatial patterns/profiles of biomaterials, porosity and/or bioactive signals. The process of making the three-dimensional tissue engineering scaffolds successfully produces porous, well-connected matrices, which may be suitable for a variety of tissue engineering applications depending on the selection of suitable biomaterial(s). The process provides excellent spatial resolution over the constituents and can be used to create a variety of gradient profiles, including linear as well as non-linear gradients. The process can be used to create porous, biocompatible and biodegradable scaffolds using microspheres made of, for example, poly(D,L-lactide-co-glycolide) (PLG). Scaffolds with predefined spatial-loaded (encapsulated or surface-immobilized) microspheres can be prepared. Additionally, porosity patterns can be created within a scaffold using microspheres of different sizes.

Scaffolds can be fabricated by flowing microsphere suspensions into a mold of pre-determined shape (to allow fabrication of shape-specific materials) with predefined flow profiles via low dead-volume tubings. The microspheres can be fused to form a continuous material with a melding agent such as ethanol, heat, or pressurized carbon dioxide. The process can utilize commercially available programmable syringe pumps for the generation of various profiles connected. Motor-driven syringe pumps have previously been used for the generation of gel-based (pH) gradients, however, with applications in electrophoresis. These types of pumps can now be used with liquid microsphere compositions to create three-dimensional tissue engineering scaffolds with various characteristics. The method of manufacturing a tissue engineering scaffold with microspheres is a novel way to synthesize the products, with diversified area of application (useful for many applications, including tissue regeneration).

Figure 1:
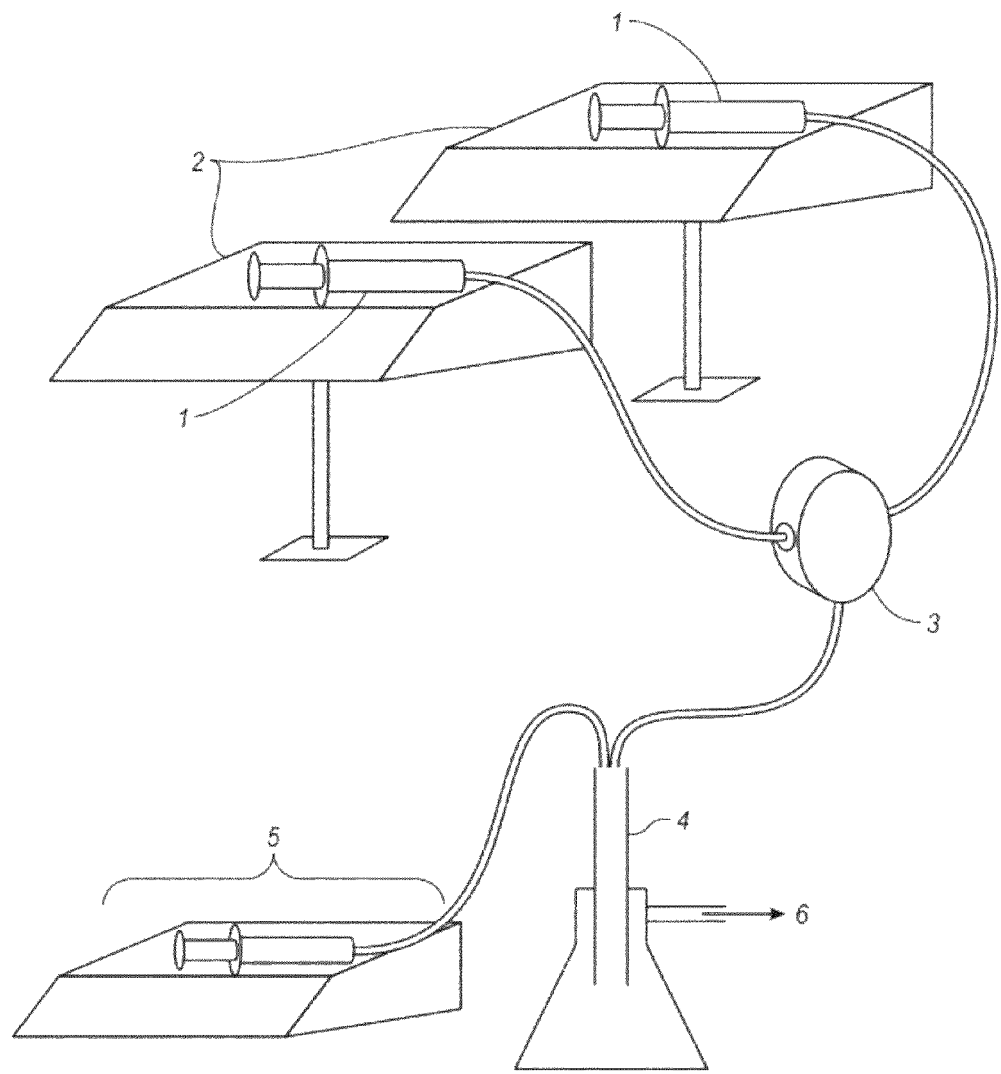
FIG. 1 illustrates a schematic representation of an embodiment of a system for preparing microsphere-based scaffolds.

FIG. 1 is a schematic diagram of an embodiment of a scaffold fabrication apparatus in accordance with the present invention. The syringes 1 containing dye-loaded or blank microsphere suspensions in distilled water/PVA solution can be attached to two programmable syringe pumps 2. The suspensions can be pumped in a predefined controlled manner through the attached tubings that join at a coupling 3 into a single tube that can be introduced to a cylindrical glass mold 4. Through the bottom of the mold 4, the distilled water/PVA solution can be constantly filtered, while the microparticles settle in the mold 4. During the entire process, the suspensions in the syringes 1 can be kept homogeneous using external magnetic stirrers (not shown). A constant level of distilled water can be maintained in the mold 4 by an infusion syringe pump 5 and a vacuum pump 6. At the end of the process, distilled water can be completely pulled out using the vacuum pump 6, leaving microparticles stacked in scaffold form in the mold 4.

The present invention can utilize microspheres to create spatial patterning of biological agents that are of special interest to investigators in areas such as nerve tissue engineering, study of chemotaxis, and the like where gradients of surface-immobilized or soluble signaling molecules have been employed. Additionally, the predetermined spatial distribution of the microspheres can be used to modulate the immune and/or inflammatory systems, and controlled spatial and temporal release of anti-inflammatories or chemokines, as desired. In addition, the predetermined spatial distribution of one or more distinct types of microspheres can be used in interfacial tissue engineering to prepare scaffolds with biphasic and gradient distributions of bioactive signals.

In addition, the methods of the present invention can be used to create three-dimensional scaffolds with spatial gradients of soluble growth factor and with controlled temporal release of soluble growth factors. In this regard, the current invention provides a novel method to achieve spatial as well as temporal control over the soluble growth factor (or other bioactive agent) release in three-dimensional scaffolds over time.

In one embodiment, the present invention utilizes growth factor-encapsulated polymeric microspheres (or other biological agent-encapsulated microspheres) as constituents, which are long known to have capability for providing controlled, sustained release. For example, an endoprosthesis can be prepared as a gradient scaffold that is made from growth factor-loaded microspheres, which may serve as novel sustained delivery devices of heterogeneous signals in a continuous and seamless manner for applications in tissue engineering. The process is capable of generating virtually any type of gradient profile. Moreover, the process has the capability to be extended to generate spatial profiles of immobilized growth factors, different polymeric biomaterials, and/or porosity patterns within a scaffold, which are of interest to tissue engineers, in general.

The three-dimensional microsphere structures can be used for the following: osteochondral defect repair (in the presence of growth factors with or without cells) and tissue engineering; axonal regeneration; study of chemotaxis in three-dimensions; directed angiogenesis; regeneration of other interfacial tissues such as muscle-bone, skin layers; temporal and spatial control of release of inflammatory and/or immune system modulators in regenerative medicine applications; and any application requiring a biocompatible, biodegradable material with spatial and temporal control over material composition, bioactive signal release, and porosity.

Microsphere-based scaffolds can provide sustained release of encapsulated growth factors, providing an edge over the soluble protein-containing gel-based scaffolds. To avoid/reduce any change in spatial signal profile, diffusion of the growth factors from the site of release can be regulated by either changing the boundary conditions (e.g., using small-sized wells during in vitro culture, etc.) or by controlling the total amount of growth factor released (balancing the generation and consumption of the growth factors transiently), or controlling the rate of release.

In addition, the microsphere-based scaffolds can be used for establishing in vivo efficacy of gradient scaffolds. For example, preliminary in vivo testing using PLG microspheres encapsulated with osteogenic chondrogenic growth factors for osteochondral defect repair has been performed. As such, the technique is flexible to construct matrices of any polymeric material of the microspheres. Therefore, choosing a microsphere suitable for a particular biomedical/tissue engineering application will eliminate any biomaterial-related concern because any microsphere can be used as appropriate.

For example, uniform PLG microspheres encapsulating fluorescent dyes can create bi-layered, multi-layered, and linear gradient scaffolds. Additionally, the scaffolds made of PLG microspheres were compatible for cell attachment and culture, and had desirable mechanical properties.

In one embodiment, the microspheres can include immobilized surface factors (e.g., RGD adhesion sequences). A distribution of microspheres having immobilized surface factors that produce a gradient of such factors can influence cell migration.

In one embodiment, the present invention includes a novel method of producing a novel composition of matter and methods of using the same. The present invention is an enhancement over other three-dimensional scaffolds by having the ability to create a microsphere-based scaffold material with spatial variation of materials and bioactive signals. Accordingly, the composition of matter has a spatially-controlled microsphere distribution with respect to the three-dimensional scaffold, which can include the spatial control of more than one type of distinct microsphere.

In one embodiment, a method for creating the microsphere-based scaffolds can be performed by flowing two or more different types of distinct microparticles (differing in material, size, encapsulated bioactive signal, and/or tethered surface bioactive signal, etc.) into a mold at desired steady or varying rates. The shape of the final scaffold is determined by the shape of the mold, which can be any desired shape, for example a cylindrical "plug" shape. The microspheres can be melded together by any desired means, including but not limited to, use of a plasticizer, solvent (e.g., ethanol) or gas (e.g., sub-critical carbon dioxide) that functions as a melding agent, high pressure with CO2, or heat sintering. Based on the controlled release from the microparticles, the design imparts the inherent temporal control of release of bioactive agents from the microsphere in order to provide an overall spatiotemporal (e.g., spatial and temporal) control. In this manner, the microsphere-based scaffolds may be utilized, for example, to provide gradients of stiffness and/or bioactive signals of any desired gradient profile (e.g., linear transition from one side to another).

The microparticle-based scaffolds can have gradients of stiffness, bioactive signals, or the like in a microsphere-based macroporous, interconnected-pore, three-dimensional matrix structure that can be biodegradable. This microsphere-based macroporous, interconnected-pore, three-dimensional matrix structure design can have broad application in several application, for example implantation (into humans or animals), with or without seeded cells, to facilitate tissue generation and/or regeneration or to provide spatiotemporal release of immune mediators.

An increase in the mechanical characteristics of the scaffolds can be achieved by microspheres with a bimodal distribution in the design of the scaffolds, which would provide additional connections between the microspheres and a closer packing.

The microsphere-based scaffold can regulate the temporal presence of growth factors by controlling their release kinetics from their carriers. Spatial control over the release of these bioactive molecules is an aspect that, along with the temporal control, that may provide the possibility of mimicking biological signal patterns, such as those during embryonic development. In the present invention, a novel scaffold fabrication apparatus (FIG. 1) can be used to prepare the microsphere-based scaffolds described herein. The apparatus demonstrated the ability to produce microsphere-based scaffolds with spatial control over molecular composition. The identification of microsphere concentration profiles were obtained using blank or dye-loaded microspheres, which were used as building blocks to fabricate bi-layered, multi-layered and gradient scaffolds.

In comparison to traditional microsphere preparation methods, the methods of the present invention provide the ability to synthesize monodispersed microspheres, which may lead to improved systems to explore the effects of microparticle size on microsphere-based scaffolds. Scaffolds made of uniform microspheres are ideal to study the influence of microparticle size on the degradation patterns and rates within scaffolds. In addition, as observed in the case of colloidal crystal-templated gel-based tissue scaffolds, uniform microspheres can pack closely compared to randomly-sized microspheres, providing better control over the pore-sizes and porosity of the scaffold, and may considerably aid the mechanical integrity of the scaffolds. Moreover, local release of molecules from the microspheres in a bulk scaffold is related to individual microsphere size and polymer properties. Reproducibility and predictability associated with uniform microsphere-based scaffolds may make them suitable for a systematic study of physical and chemical effects in order to achieve control over local release of growth factor within such a scaffold.

Integrated microsphere matrices have been created in the past by employing a heat-sintering technique, which requires heating of microspheres above their glass transition temperatures (Tg). Heat sintering is not suitable for the preparation of bioconductive microsphere-based scaffolds. The inclusion of proteins, polypeptides, nucleic acids, genes viral vectors, small molecules, drugs, antibodies, and growth factors in the microspheres before exposing them to heat may severely affect activity. The sintering temperatures and durations of heat exposure used in some previous studies were 160° C. for 4 h (PLG; 85:15 lactic acid:glycolic acid), 65° C. for 4 h (PLG/bioactive glass), 70° C. for 4 h (poly(D,L-lactide)/poly (ethylene glycol)), and 62° C. for varied times of 4, 24, 48 and 72 h (PLG; 58:42 lactic acid:glycolic acid). Such elevated temperatures for extended durations can lead to reduction in the bioactivity or complete denaturation of encapsulated therapeutic agents, such as nucleic acids and proteins, which has earlier been commented as a concern for the production of matrices made of growth factor-loaded microspheres.

In the present invention, a novel ethanol-melding technique can be used to create interconnected microsphere matrices, which may alleviate concerns of reduced bioactivity from microsphere-based matrices. When compared to heat sintering of PLG microspheres, the process of ethanol melding can result in matrices of lower compressive stiffness. The range of average compressive moduli, reported in a previous study employing heat sintering at 62° C. for 24 h, was 241 to 349 MPa, which was significantly higher than the moduli reported herein. However, the reported porosity of the resulting scaffolds ranged from 32-39%, which were significantly lower than the porosities reported herein. However lower or higher porosities can be obtained by modulating the size of microspheres used as well as the size distribution of microspheres and the duration of melding. As the porosities of such microsphere-based matrices reflect the extent of fusion of the adjacent microspheres within a given matrix, the differences in the porosities may explain the differences observed in the macro-mechanical properties. Increasing ethanol-soak time, changing the microsphere size, or providing microspheres of different sizes may lead to improved mechanical characteristics and, may be used to modulate scaffold porosity.

The effect of ethanol melding on the glass transition temperature (Tg) of the raw PLG can be determined. It was found that the Tg can drop below 37° C., which may affect the mechanical properties of the scaffolds when placed in vivo. To keep the Tg of the scaffolds above the limit of 37° C., the use of PLG with higher molecular weights, crosslinking, different sized microspheres, or PLG with a higher lactic acid to glycolic acid ratios can be used. Also, the microspheres can be doped with polymers or the materials or formed as copolymers that have higher glass transition temperatures.

The present invention provides a manufacturing system and methods for manufacturing microparticle-based gradient scaffolds. The scaffolds can be designed to release opposing gradients of bioactive signals (e.g., biological proteins) at the interface of a biphasic tissue engineering scaffold. The methodology may also be extended to create biphasic scaffolds with more than two growth factors or multi-phasic scaffold with more than one interface. The use of ethanol, acetone, or other solvent or media (e.g., carbon dioxide) as a melding agent can create interconnected microsphere-based matrices, for encapsulated, thermally labile bioactive molecules. For example, growth factor-loaded microspheres may be used to create similar heterogeneous three-dimensional scaffolds to deliver growth factors with pre-defined spatial and temporal release profiles. Also, the scaffolds can be prepared as seamless gradient scaffolds, bi-layered scaffolds, or the like for osteochondral tissue regeneration.

In one embodiment, the microsphere-based scaffolds can be used in osteochondral tissue engineering. As such, the scaffolds can be used to prepare cartilage, bond, or a junction of cartilage and bone by use of heterogeneous signals provided by the use of two or more microspheres having two or more active agents for use in osteochondral tissue engineering. The use of heterogeneous signals can provide mutually inductive signals that are important for the formation of the bone and/or cartilage.

In one embodiment, the microsphere-based scaffolds can be prepared from PLG or PLGA microspheres. However the microspheres can be prepared from substantially any polymer, such as biocompatible, bioerodable, and/or biodegradable polymers. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanhydrides, polyphosphazenes, poly(phosphoesters), polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), poly(L-lysine), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), poly(anhydride-co-imides), poly(amides), poly(iminocarbonates), poly(urethanes), poly(organophasphazenes), poly(phosphates), poly(ethylene vinyl acetate) and other acyl substituted cellulose acetates and derivatives thereof, poly(amino acids), poly(acrylates), polyacetals, poly (cyanoacrylates), poly(styrenes), poly(vinyl chloride), poly (vinyl fluoride), poly(vinyl imidazole), chlorosulfonated polyolefins, polyethylene oxide, combinations thereof, polymers having monomers thereof, or the like. In certain preferred aspects, the nano-particles include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, etc. and their derivatives, co-polymers, and mixtures thereof. A non-limiting method for making nano-particles is described in U.S. Publication 2003/0138490, which is incorporated by reference.

The methods of making the scaffolds from the microspheres can be changed to include a solvent or solvent system (i.e., media or media system) that is compatible with the particular polymer of the microsphere. That is, the solvent or solvent system can be selected to meld the microspheres together as described herein. Examples of some solvents can include hexane, benzene, toluene, diethyl ether, chloroform, ethyl acetate, 1,4-dioxane, tetrahydrofuran, dichloromethane, acetone, acetonitrile, dimethylformamide, dimethyl sulfoxide, acetic acid, n-butanol, 2-butanol, 3-butanol, t-butyl alcohol, carbon tetrachloride, chlorobenzene, isopropanol, n-propanol, ethanol, methanol, formic acid, water, cyclohexane, 1,2-dichloroethane, diethyl ether, diethylene glycol, diglyme, dimethyl ether, dioxane, ethylene glycol, glycerin, heptane, hexamethylphosphoramide, hexamethylphosphorous triamide, hexane, nitromethane, pentane, petroleum ether, propanol, pyridine, o-xylene, m-xylene, p-xylene, and the like. Carbon dioxide can also be used as a solvent or media to meld the microspheres together. Also, solvents known for particular polymers can be used or combined with the solvents described herein.

The scaffolds can be prepared to contain and release substantially any therapeutic agent. Examples of some pharmaceutics agents that be useful in scaffolds for use in a body lumen, such as a blood vessel can include: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) II b/III a inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chloro deoxyadeno sine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives e.g., aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors; β2 agonists (e.g. salbutamol, terbutaline, clenbuterol, salmeterol, formoterol); steroids such glycocorticosteroids, preferably anti-inflammatory drugs (e.g. Ciclesonide, Mometasone, Flunisolide, Triamcinolone, Beclomethasone, Budesonide, Fluticasone); anticholinergic drugs (e.g. ipratropium, tiotropium, oxitropium); leukotriene antagonists (e.g. zafirlukast, montelukast, pranlukast); xantines (e.g. aminophylline, theobromine, theophylline); Mast cell stabilizers (e.g. cromoglicate, nedocromil); inhibitors of leukotriene synthesis (e.g. azelastina, oxatomide ketotifen); mucolytics (e.g. N-acetylcysteine, carbocysteine); antibiotics, (e.g. Aminoglycosides such as, amikacin, gentamicin, kanamycin, neomycin, netilmicin streptomycin, tobramycin; Carbacephem such as loracarbef, Carbapenems such as ertapenem, imipenem/cilastatin meropenem; Cephalosporins-first generation—such as cefadroxil, cefaxolin, cephalexin; Cephalosporins-second generation—such as cefaclor, cefamandole, defoxitin, cefproxil, cefuroxime; Cephalosporins-third generation-cefixime, cefdinir, ceftaxidime, defotaxime, cefpodoxime, ceftriaxone; Cephalosporins—fourth generation—such as maxipime; Glycopeptides such as vancomycin, teicoplanin; Macrolides such as azithromycin, clarithromycin, Dirithromycin, Erythromycin, troleandomycin; Monobactam such as aztreonam; Penicillins such as Amoxicillin, Ampicillin, Azlocillin, Carbenicillin, Cloxacillin, Dicloxacillin, Flucloxacillin, Mezlocillin, Nafcillin, Penicillin, Piperacillin, Ticarcillin; Polypeptides such as bacitracin, colistin, polymyxin B; Quinolones such as Ciprofloxacin, Enoxacin, Gatifloxacin, Levofloxacin, Lomefloxacin, Moxifloxacin, Norfloxacin, Ofloxacin, Trovafloxacin; Sulfonamides such as Mafenide, Prontosil, Sulfacetamide, Sulfamethizole, Sulfanilimide, Sulfasalazine, Sulfisoxazole, Trimethoprim, Trimethoprim-Sulfamethoxazole Co-trimoxazole (TMP-SMX); Tetracyclines such as Demeclocycline, Doxycycline, Minocycline, Oxytetracycline, Tetracycline; Others such as Chloramphenicol, Clindamycin, Ethambutol, Fosfomycin, Furazolidone, Isoniazid, Linezolid, Metronidazole, Nitrofurantoin, Pyrazinamide, Quinupristin/Dalfopristin, Rifampin, Spectinomycin); pain relievers in general such as analgesic and antiinflammatory drugs, including steroids (e.g. hydrocortisone, cortisone acetate, prednisone, prednisolone, methylprednisolone, dexamethasone, betamethasone, triamcinolone, beclometasone, fludrocortisone acetate, deoxycorticosterone acetate, aldosterone); and non-steroid antiinflammatory drugs (e.g. Salicylates such as aspirin, amoxiprin, benorilate, coline magnesium salicylate, diflunisal, faislamine, methyl salicylate, salicyl salicylate); Arylalkanoic acids such as diclofenac, aceclofenac, acematicin, etodolac, indometacin, ketorolac, nabumetone, sulindac tolmetin; 2-Arylpropionic acids (profens) such as ibuprofen, carprofen, fenbufen, fenoprofen, flurbiprofen, ketoprofen, loxoprofen, naproxen, tiaprofenic acid; N-arylanthranilic acids (fenamic acids) such as mefenamic acid, meclofenamic acid, tolfenamic acid; Pyrazolidine derivatives such as phenylbutazone, azapropazone, metamizole, oxyphenbutazone; Oxicams such as piroxicam, meloxicam, tenoxicam; Coxib such as celecoxib, etoricoxib, lumiracoxib, parecoxib, rofecoxib (withdrawn from market), valdecoxib (withdrawn from market); Sulphonanilides such as nimesulide; others such as licofelone, omega-3 fatty acids; cardiovascular drugs such as glycosides (e.g. strophantin, digoxin, digitoxin, proscillaridine A); respiratory drugs; antiasthma agents; bronchodilators (adrenergics: albuterol, bitolterol, epinephrine, fenoterol, formoterol, isoetharine, isoproterenol, metaproterenol, pirbuterol, procaterol, salmeterol, terbutaline); anticancer agents (e.g. cyclophosphamide, doxorubicine, vincristine, methotrexate); alkaloids (i.e. ergot alkaloids) or triptans such as sumatriptan, rizatriptan, naratriptan, zolmitriptan, eletriptan and almotriptan, than can be used against migraine; drugs (i.e. sulfonylurea) used against diabetes and related dysfunctions (e.g. metformin, chlorpropamide, glibenclamide, glicliazide, glimepiride, tolazamide, acarbose, pioglitazone, nateglinide, sitagliptin); sedative and hypnotic drugs (e.g. Barbiturates such as secobarbital, pentobarbital, amobarbital; uncategorized sedatives such as eszopiclone, ramelteon, methaqualone, ethchlorvynol, chloral hydrate, meprobamate, glutethimide, methyprylon); psychic energizers; appetite inhibitors (e.g. amphetamine); antiarthritis drugs (NSAIDs); antimalaria drugs (e.g. quinine, quinidine, mefloquine, halofantrine, primaquine, cloroquine, amodiaquine); antiepileptic drugs and anticonvulsant drugs such as Barbiturates, (e.g. Barbexaclone, Metharbital, Methylphenobarbital, Phenobarbital, Primidone), Succinimides (e.g. Ethosuximide, Mesuximide, Phensuximide), Benzodiazepines, Carboxamides (e.g. Carbamazepine, Oxcarbazepine, Rufinamide) Fatty acid derivatives (e.g. Valpromide, Valnoctamide); Carboxilyc acids (e.g. Valproic acid, Tiagabine); Gaba analogs (e.g. Gabapentin, Pregabalin, Progabide, Vigabatrin); Topiramate, Ureas (e.g. Phenacemide, Pheneturide), Carbamates (e.g. emylcamate Felbamate, Meprobamate); Pyrrolidines (e.g. Levetiracetam Nefiracetam, Seletracetam); Sulfa drugs (e.g. Acetazolamide, Ethoxzolamide, Sultiame, Zonisamide) Beclamide; Paraldehyde, Potassium bromide; antithrombotic drugs such as Vitamin K antagonist (e.g. Acenocoumarol, Dicumarol, Phenprocoumon, Phenindione, Warfarin); Platelet aggregation inhibitors (e.g. antithrombin III, Bemiparin, Deltaparin, Danaparoid, Enoxaparin, Heparin, Nadroparin, Pamaparin, Reviparin, Tinzaparin); Other platelet aggregation inhibitors (e.g. Abciximab, Acetylsalicylic acid, Aloxiprin, Ditazole, Clopidogrel, Dipyridamole, Epoprostenol, Eptifibatide, Indobufen, Prasugrel, Ticlopidine, Tirofiban, Treprostinil, Trifusal); Enzymes (e.g. Alteplase, Ancrod, Anistreplase, Fibrinolysin, Streptokinase, Tenecteplase, Urokinase); Direct thrombin inhibitors (e.g. Argatroban, Bivalirudin. Lepirudin, Melagatran, Ximelagratan); other antithrombotics (e.g. Dabigatran, Defibrotide, Dermatan sulfate, Fondaparinux, Rivaroxaban); antihypertensive drugs such as Diuretics (e.g. Bumetanide, Furosemide, Torsemide, Chlortalidone, Hydroclorothiazide, Chlorothiazide, Indapamide, metolaxone, Amiloride, Triamterene); Antiadrenergics (e.g. atenolol, metoprolol, oxprenolol, pindolol, propranolol, doxazosin, prazosin, teraxosin, labetalol); Calcium channel blockers (e.g. Amlodipine, felodipine, dsradipine, nifedipine, nimodipine, diltiazem, verapamil); Ace inhibitors (e.g. captopril, enalapril, fosinopril, lisinopril, perindopril, quinapril, ramipril, benzapril); Angiotensin II receptor antagonists (e.g. candesartan, irbesartan, losartan, telmisartan, valsartan); Aldosterone antagonist such as spironolactone; centrally acting adrenergic drugs (e.g. clonidine, guanabenz, methyldopa); antiarrhythmic drug of Class I that interfere with the sodium channel (e.g. quinidine, procainamide, disodyramide, lidocaine, mexiletine, tocamide, phenyloin, encamide, flecamide, moricizine, propafenone), Class II that are beta blockers (e.g. esmolol, propranolol, metoprolol); Class III that affect potassium efflux (e.g. amiodarone, azimilide, bretylium, clorilium, dofetilide, tedisamil, ibutilide, sematilide, sotalol); Class IV that affect the AV node (e.g. verapamil, diltiazem); Class V unknown mechanisms (e.g. adenoide, digoxin); antioxidant drugs such as Vitamin A, vitamin C, vitamin E, Coenzime Q10, melanonin, carotenoid terpenoids, non carotenoid terpenoids, flavonoid polyphenolic; antidepressants (e.g. mirtazapine, trazodone); antipsychotic drugs (e.g. fluphenazine, haloperidol, thiotixene, trifluoroperazine, loxapine, perphenazine, clozapine, quetiapine, risperidone, olanzapine); anxyolitics (Benzodiazepines such as diazepam, clonazepam, alprazolam, temazepam, chlordiazepoxide, flunitrazepam, lorazepam, clorazepam; Imidaxopyridines such as zolpidem, alpidem; Pyrazolopyrimidines such as zaleplon); antiemetic drugs such as Serotonine receptor antagonists (dolasetron, granisetron, ondansetron), dopamine antagonists (domperidone, droperidol, haloperidol, chlorpromazine, promethazine, metoclopramide) antihystamines (cyclizine, diphenydramine, dimenhydrinate, meclizine, promethazine, hydroxyzine); antiinfectives; antihystamines (e.g. mepyramine, antazoline, diphenihydramine, carbinoxamine, doxylamine, clemastine, dimethydrinate, cyclizine, chlorcyclizine, hydroxyzine, meclizine, promethazine, cyproheptadine, azatidine, ketotifen, acrivastina, loratadine, terfenadine, cetrizidinem, azelastine, levocabastine, olopatadine, levocetrizine, desloratadine, fexofenadine, cromoglicate nedocromil, thiperamide, impromidine); antifungus (e.g. Nystatin, amphotericin B., natamycin, rimocidin, filipin, pimaricin, miconazole, ketoconazole, clotrimazole, econazole, mebendazole, bifonazole, oxiconazole, sertaconazole, sulconazole, tiaconazole, fluconazole, itraconazole, posaconazole, voriconazole, terbinafine, amorolfine, butenafine, anidulafungin, caspofungin, flucytosine, griseofulvin, fluocinonide) and antiviral drugs such as Anti-herpesvirus agents (e.g. Aciclovir, Cidofovir, Docosanol, Famciclovir, Fomivirsen, Foscarnet, Ganciclovir, Idoxuridine, Penciclovir, Trifluridine, Tromantadine, Valaciclovir, Valganciclovir, Vidarabine); Anti-influenza agents (Amantadine, Oseltamivir, Peramivir, Rimantadine, Zanamivir); Antiretroviral drugs (abacavir, didanosine, emtricitabine, lamivudine, stavudine, tenofovir, zalcitabine, zidovudine, adeforvir, tenofovir, efavirenz, delavirdine, nevirapine, amprenavir, atazanavir, darunavir, fosamprenavir, indinavir, lopinavir, nelfinavir, ritonavir, saquinavir, tipranavir); other antiviral agents (Enfuvirtide, Fomivirsen, Imiquimod, Inosine, Interferon, Podophyllotoxin, Ribavirin, Viramidine); drugs against neurological dysfunctions such as Parkinson's disease (e.g. dopamine agonists, L-dopa, Carbidopa, benzerazide, bromocriptine, pergolide, pramipexole, ropinipole, apomorphine, lisuride); drugs for the treatment of alcoholism (e.g. antabuse, naltrexone, vivitrol), and other addiction forms; vasodilators for the treatment of erectile dysfunction (e.g. Sildenafil, vardenafil, tadalafil), muscle relaxants (e.g. benzodiazepines, methocarbamol, baclofen, carisoprodol, chlorzoxazone, cyclobenzaprine, dantrolene, metaxalone, orphenadrine, tizanidine); muscle contractors; opioids; stimulating drugs (e.g. amphetamine, cocaina, caffeine, nicotine); tranquillizers; antibiotics such as macrolides; aminoglycosides; fluoroquinolones and β-lactames; vaccines; cytokines; growth factors; hormones including birth-control drugs; sympathomimetic drugs (e.g. amphetamine, benzylpiperazine, cathinone, chlorphentermine, clobenzolex, cocaine, cyclopentamine, ephedrine, fenfluramine, methylone, methylphenidate, Pemoline, phendimetrazine, phentermine, phenylephrine, propylhexedrine, pseudoephedrine, sibutramine, symephrine); diuretics; lipid regulator agents; antiandrogen agents (e.g. bicalutamide, cyproterone, flutamide, nilutamide); antiparasitics; blood thinners (e.g. warfarin); neoplastic drugs; antineoplastic drugs (e.g. chlorambucil, chloromethine, cyclophosphamide, melphalan, carmustine, fotemustine, lomustine, carboplatin, busulfan, dacarbazine, procarbazine, thioTEPA, uramustine, mechloretamine, methotrexate, cladribine, clofarabine, fludarabine, mercaptopurine, fluorouracil, vinblastine, vincristine, daunorubicin, epirubicin, bleomycin, hydroxyurea, alemtuzumar, cetuximab, aminolevulinic acid, altretamine, amsacrine, anagrelide, pentostatin, tretinoin); hypoglicaemics; nutritive and integrator agents; growth integrators; antienteric drugs; vaccines; antibodies; diagnosis and radio-opaque agents; or mixtures of the above mentioned drugs (e.g. combinations for the treatment of asthma containing steroids and β-agonists); or any other biologically active agent such as nucleic acids, DNA, RNA, siRNA, polypeptides, antibodies, and the like. Growth factors and adhesion peptides can be useful for tissue development within a subject and can be included in the microspheres.

The microsphere-based scaffold can be prepared into substantially any shape by preparing a mold to have the desired shape. For example, the microsphere-based scaffold can be prepared into the shapes of rods, plates, spheres, wrappings, patches, plugs, depots, sheets, cubes, blocks, bones, bone portions, cartilage, cartilage portions, implants, orthopedic implants, orthopedic screws, orthopedic rods, orthopedic plates, and the like. Also, the microsphere-based scaffolds can be prepared into shapes to help facilitate the transitions between tissues, such as between bone to tendon, bone to cartilage, tendon to muscle, dentin to enamel, skin layers, disparate layers, and the like. The microsphere-based scaffolds can also be shaped as bandages, plugs, or the like for wound healing.

In one embodiment, the mean theoretical porosities of the scaffolds can have a range between about 10 to about 95, more preferably about 40 to about 40, and most preferably from about 45 to about 50. An example of porosity is about 44.9% to about 49%.

The scaffolds can have pore sizes ranging from about 200 um to about 1650 um. For cartilage tissue engineering, the pore sizes can be from about 70 um to about 120 um. In bone tissue engineering, pore sizes as small as about 50 um or larger can be used. Although optimal pore sizes can be within a range of about 100 um to about 600 um.

In one embodiment, the mean particle size of the microspheres used to prepare the scaffolds can have a range between about less than about 1 um to about greater than 1 mm, more preferably about 100 um (e.g., um is microns) to about 300 um, and most preferably from about 180 to about 240 um. An example of particle size is about 180 μm to about 220 μm.

In one embodiment, the average moduli of elasticity of the scaffolds can have a range between about 6 kPa to about 40 MPa, more preferably about 200 kPa to about 8 MPa, and most preferably from about 1 MPa to about 4 MPa. Examples of elasticity can be about 4.2 MPa to about 6.0 MPa or about 5 MPa to about 12 MPa.

Figure 8:
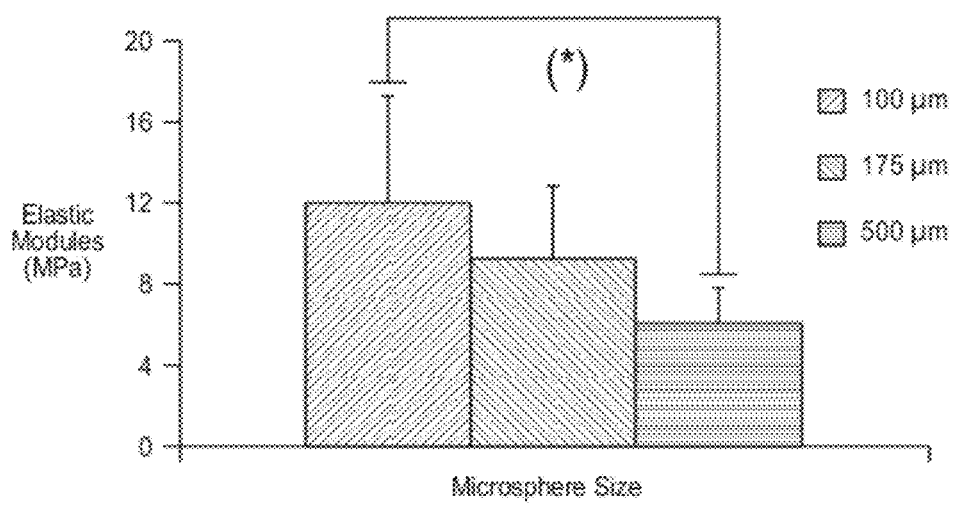
FIG. 8 is a graph illustrating the elastic modulus with respect to microsphere size.

In one embodiment, the microspheres and/or microsphere-based scaffolds can be processed with nanophase CaCO3 to produce a nanophase within the microsphere that hardens the microspheres and resulting microsphere-based scaffolds. Nanophase CaCO3 has been found to improve stiffness of microspheres by 2-8 times. FIG. 8 is a graph that shows the elastic modulus at high strains of microspheres of 100 um, 175 um, and 500 um. Accordingly, the stiffness of the microspheres can be modulated to obtain a stiffness of the scaffold to have a range between about 6 kPa to about 40 MPa, more preferably about 200 kPa to about 8 MPa, and most preferably from about 1 MPa to about 4 MPa. Also, the amount of CaCO3 (or any nanophase material) can have a range between about 0 to about 50% by weight, more preferably about 5% to about 30%, and most preferably from about 5% to about 20%. Numerous other materials can be used as a nanophase material to be included in the microspheres, including but not limited to titanium oxide or hydroxyapatite.

In one embodiment, the glass transition temperature of the scaffolds can have a range between about 30° C. to about 65° C., more preferably about 32° C. to about 50° C., and most preferably from about 34° C. to about 42° C. Examples of glass transition temperature can be about 36° C. to about 38° C.

In one embodiment, the microsphere-based scaffold can be prepared to have a mechanical property gradient. For example, one side can be stiffer and the other side can be softer. This can be accomplished by using microspheres with different mechanical properties. Gradients in mechanical properties in native tissues often exist within and between the tissues, which help in avoiding stress concentrations, such as cartilage, human crystalline lens, and the dentin-enamel junction. Studies have recently confirmed that cells sense and respond to the stiffness of their surrounding environment, influencing lineage commitment as well as migration and proliferation. Mesenchymal stem cells can be directed toward neurogenic (soft matrices), myogenic (intermediate stiffness), or osteogenic (high stiffness) lineages based on the stiffness of the surrounding matrix. Thus, a 3D stiffness gradient can be useful, and can be tailored to match bone and cartilage moduli. As such, an appropriate range can be provide for a scaffold construct with mechanical integrity sufficient for gradual increase in weight bearing (e.g., from gentle walking eventually up to active movement) as the construct in the animal or patient remodels and ultimately matches the native tissue. For example, a range of moduli in osteochondral constructs can be about 10 MPa for cartilage and about 50 MPa for bone.

In one embodiment, the microsphere-based scaffold can be prepared with a sub-critical carbon dioxide (CO2) technique. Sub-critical CO2 is not toxic and can be used in place of organic solvents. Accordingly, poly(lactic-co-glycolic acid) microspheres of three different sizes (e.g., 100 um, 175, um, and 500 um) can be prepared. The microsphere-based scaffolds can be prepared by melding the microspheres together in a high pressure chamber at sub-critical pressures of CO2. For example, sub-critical pressures can be 165 psi, 190 psi, and 220 psi, or any range therebetween. However, higher pressures can be used for larger microspheres, and lower pressures for smaller microspheres.

Accordingly, shape-specific, macroporous tissue engineering scaffolds can be fabricated and homogeneously seeded with cells in a single step. This method brings together CO2 polymer processing and microparticle-based scaffolds in a manner that allows each to solve the key limitation of the other. Specifically, microparticle-based scaffolds prepared from conventional microsphere sintering methods (e.g., heat, solvents) are not cytocompatible. That is, the microspheres cannot be melded together in the presence of live cells without killing the cells. However, it has now been found that cells can be included with the microspheres during the melding process when melded with CO2. Accordingly, it has been shown that cell viability can be sustained with sub-critical (i.e., gaseous) CO2 sintering of microspheres in the presence of cells at near-ambient temperatures. The scaffolds prepared with CO2 also retain the pore structures described herein. On the other hand, pore interconnectivity has eluded supercritical CO2 foaming approaches. The fused poly(lactide-co-glycolide) microsphere scaffolds can be seeded with any type of cell, such as human umbilical cord mesenchymal stromal cells. Accordingly, the scaffolds can be used for cartilage regeneration, or any tissue engineering application such as those described herein.

In one embodiment, the microsphere scaffolds can be prepared with a liquid medium in the presence of CO2 in order to produce thin sheet of melded microspheres. The liquid medium can retain the individual microspheres internally, and only the external surface microspheres are melded together to provide the thin sheet. Also, cells can be loaded in the thin sheet of microspheres with the CO2 and liquid medium process. The thin sheets of melded microspheres, such as the cell-loaded sheets, can be used as patches in skin tissue engineering and wound healing applications.

Gaseous $CO_2$ sintering can be used to fabricate cell-seeded, microsphere-based, shape-specific constructs in a single step. These constructs can retain the numerous advantages of microsphere-based scaffolds such as spatiotemporal control for creating 3D signal and stiffness gradients for interfacial tissue engineering within a single scaffold. The resulting scaffolds were porous, exhibited moduli similar to the native cartilaginous tissues, and displayed support for chondrogenesis and cartilage-like tissue growth. The process of sub-critical $CO_2$ sintering is also amenable to produce cell-containing matrices under relatively mild conditions. The ability to create cell-loaded scaffolds and patches may have important implications for cartilage and skin tissue engineering, respectively, where growth factor-encapsulated microspheres can be used to design cell-loaded controlled release vehicles in a single-step as a regenerative protocol.

In one embodiment, the present invention may be used in connection with a diverse type of eukaryotic host cells from a diverse set of species of the plant and animal kingdoms. Preferably, the host cells are from mammalian species including cells from humans, other primates, horses, pigs, and mice. For example, cells can be stem cells of any kind (e.g., umbilical cord or placenta derived, dental pulp derived, marrow-derived, adipose derived, induced stem cells, or cells of embryonic or amniotic origin), PER.C6 cells, HT-29 cells, LNCaP-FGC cells A549 cells, MDA-MB453 cells, HepG2 cells, THP-1 cells, miMCD-3 cells, HEK 293 cells, HeLaS3 cells, MCF7 cells, Cos-7 cells, CHO cells and CHO derivatives, CHO-K1 cells, BxPC-3 cells, DU145 cells, Jurkat cells, PC-3 cells, Capan-1 cells, HuVEC cells, HuASMC cells, HKB-11 human differentiated stem cells such as osteoblasts and adipocytes from hMSC; human adherent cells such as SH-SY5Y, IMR32, LAN5, HeLa, MCF10A, 293T, and SK-BR3; primary cells such as HUVEC, HUASMC, and hMSC;

and other species such as 3T3 NIH, 3T3 L1, ES-D3, C2C12, H9c2 and the like. Additionally, any species of plant may be used. Any of these cells can be included with the microspheres when using the carbon dioxide process (e.g., single step) for preparing the scaffolds.

Figure 7A:
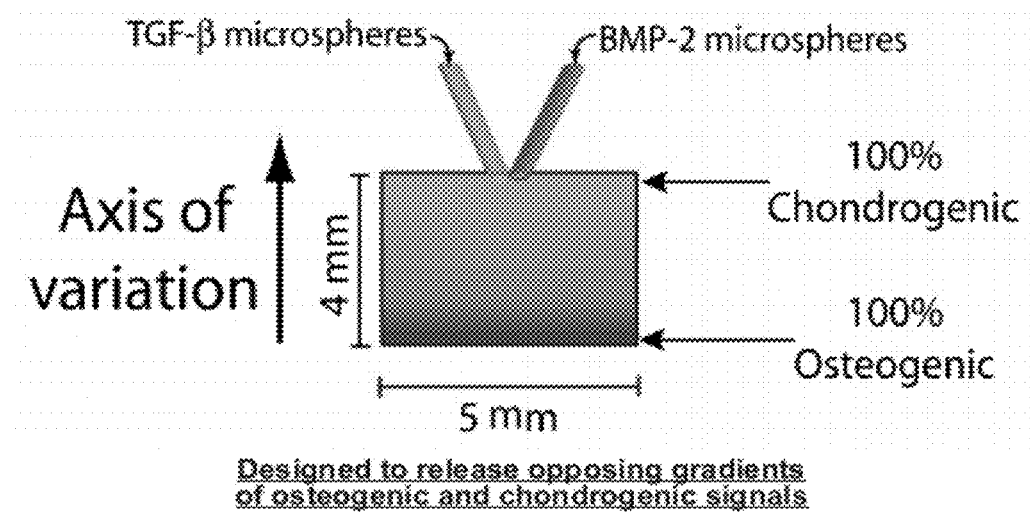
FIG. 7A is a schematic representation of a microsphere-based scaffold having TGF-beta and BMP-2 so as to be 100% chondrogenic at one end and 100% osteogenic at the other end.
Figure 7B:
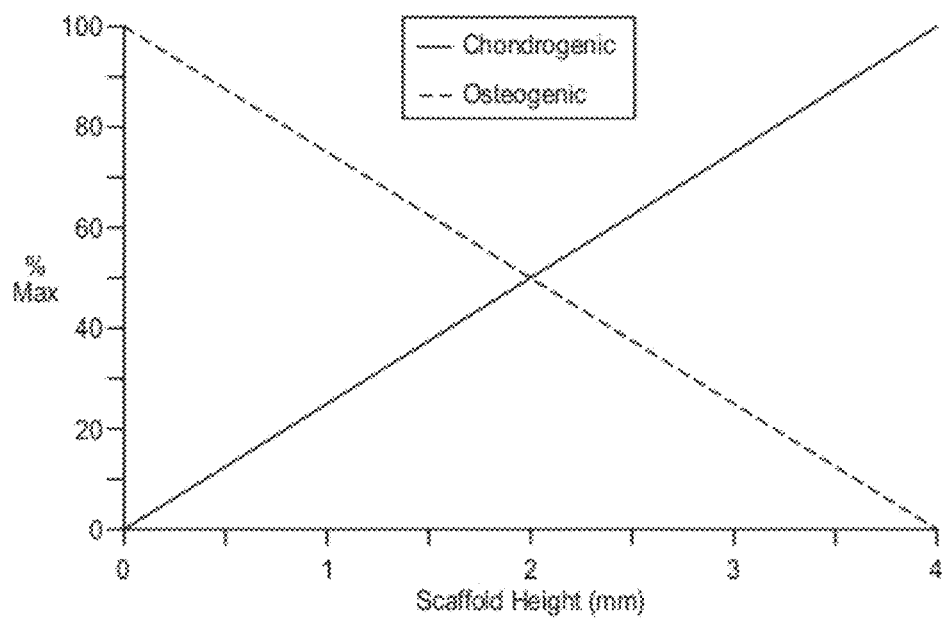
FIGS. 7B and 7C are graphical representations of possible percent chondrogenic and osteogenic gradients with respect to a microsphere-based scaffold.
Figure 7C:
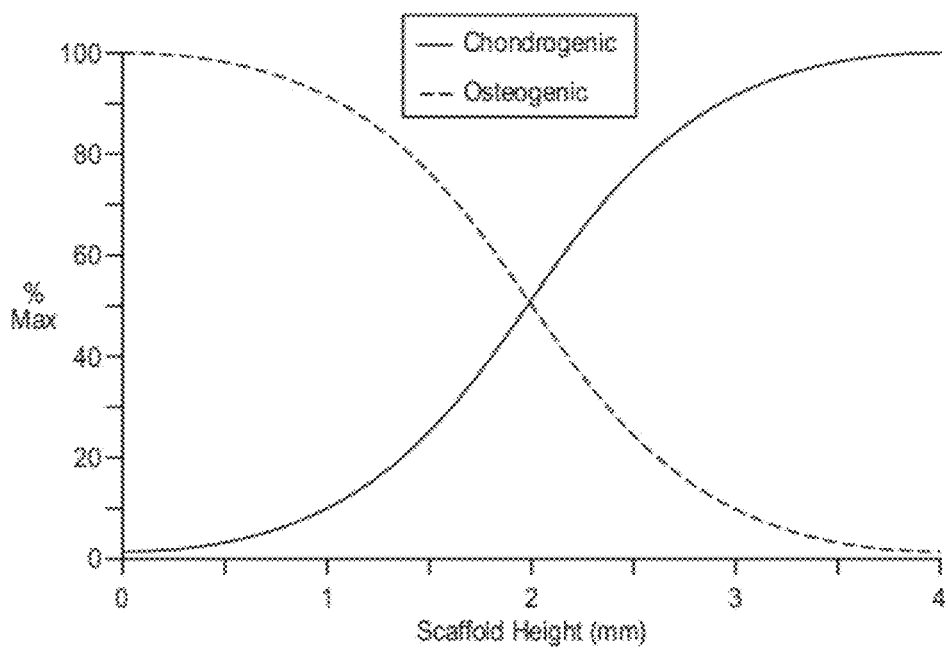

In one embodiment, the microsphere-based scaffold can be prepared to have a gradient of TGF-beta microspheres and another gradient of BMP-2 microspheres, such as is shown in FIG. 7A. As shown, the top of the scaffold is substantially 100% chondrogenic and the bottom of the scaffold is 100% osteogenic. FIG. 7B shows the concentration profile of chondrogenic and osteogenic signals. FIG. 7C shows another concentration profile that can be achieved. Also, the microspheres can use transforming growth factor-beta1 ($TGF-\beta_1$) and $TGF-\beta_3$ as competing chondrogenic factors, and BMP-2 as the osteogenic factor. In vitro rBMSC chondrogenic differentiation was well demonstrated with the stimulation of $TGF-\beta_1$ and/or dexamethasone in cell aggregates and cell pellets. Like $TGF-\beta_1$, $TGF-\beta_3$ is another known chondrogenic factor, which has been used to promote chondrogenic differentiation of BMSCs in many tissue engineering investigations. $TGF-\beta$ concentrations in vitro have been commonly prescribed between 5 and 20 ng/mL with different adult stem cells. The concentration of $TGF-\beta_1$ used in vivo, however, varies greatly (0.8 to 100 ng per scaffold, ~4 to 30 ng/mg of carrier). BMP-2 has been extensively applied as an osteogenic factor in bone tissue engineering investigations. Concentrations of BMPs applied in vivo for bone defect repair were usually higher (~1.6 to 5 μg per mg of polymer) when compared to concentrations of $TGF-\beta_1$. Rather than culture disparate cartilaginous and osseous components together in hopes of eventual integration, the microsphere-based scaffolds can provide signal gradients can directly lead to a continuous and seamless transition from cartilage to bone. Also, a signal or combination of signals (e.g., biological molecules) for cartilage to differentiate into its three layers (superficial, middle, deep) can be used in a signal gradient of chondrogenic factors and of bone-generated factors.

In one embodiment, the microsphere-based scaffold can be used in an aerospace application. For example, in applications where a transition from ceramic heat resistance to metallic mechanical integrity is required.

In one embodiment, the microsphere-based scaffold can be used for nerve regeneration. For example, nerve regeneration and axon guidance are heavily influenced by stiffness gradients and signal gradients, which can be provided by these scaffolds.

In one embodiment, the microsphere-based scaffold can be used for craniofacial and orthopedic applications. For example, any instance where there is an interface and thus a graded transition from one tissue type to another (e.g., ligament to bone, tendon to muscle, cartilage to bone, dentin to enamel, etc.), the scaffolds would be well-suited for a seamless transition from one tissue type to another.

In one embodiment, the microsphere-based scaffold can be used as an integrated osteochondral plug. Orthopedic surgeons can implant such a plug in a minimally invasive manner (arthroscope), with or without marrow or umbilical cord cells, to accelerate healing and allow osteoarthritis and impact-injury patients to return to load-bearing activities sooner. Conventional biodegradable plugs currently used have no bioactive signals to accelerate regeneration and do not account for the contrasting mechanical demands of the cartilage and underlying bone. More importantly, the microsphere-based scaffold technology is not limited to osteochondral applications, and can be used in any application where a gradient or integrated interface is desired, such as nerve regeneration, the ligament/bone interface, and the like.

In one embodiment, the microsphere-based scaffold can be prepared with microspheres that include a core and one or more shells. Microspheres with core/shell configurations can be prepared by standard techniques. The core/shell configuration can allow for customized bioactive agent release profiles. For example, the shell can be configured to have one release rate and the core can have a second release rate. Also, the core can have a different bioactive agent compared to the shell. When multiple shells are used, the different shells can have different release rates and/or different bioactive agents.

In one embodiment, the microsphere scaffolds can be prepared as a thin sheet. It has been found that when a medium is used in the carbon dioxide melding process, the liquid can keep the microspheres from melding in the bulk, but the surface microspheres meld in the presence of $CO_2$. The presence of a liquid (e.g., cells suspended in medium) provides a different result compared to when the liquid volume is minimized (e.g., cell pellet combined with microparticles). With the liquid, the $CO_2$ can only effectively penetrates the top layer. This results in only the top layer being sintered, resulting in a thin, pliable, cell-seeded polymer. However, cells do not need to be included in the medium, and the resulting thin sheet scaffold can be cell-free. In contrast, the other route provides a heterogeneously seeded construct comparable to the ethanol (or otherwise)-sintered constructs, with the key difference being that the ethanol (or otherwise)-sintered constructs would need to be seeded with cells after the scaffold fabrication, as a separate step. For example, the thin patch can be ideal for skin regeneration (e.g., burn victims). Sub-critical or gaseous $CO_2$ exposure (e.g., pressure about 15-20 bar) can be used to produce regular or intricate-shaped scaffolds.

When polymers are in the presence of $CO_2$ as a liquid (e.g., high pressure) or in a supercritical state, a foamed scaffold with non-interconnected pores is formed. However, when microspheres are melded with $CO_2$ as described herein, pore interconnectivity is obtained as shown and described. Moreover, the $CO_2$ at mild pressures is a gaseous sub-critical $CO_2$, which results in milder, and thus likely more cell-compatible conditions. Thus, microsphere sintering can now take place in the presence of cells, made possible with gaseous sub-critical $CO_2$ in mild conditions.

II. Experimental Section

1. Materials

Poly(D,L-lactide-co-glycolide) copolymer (50:50 lactic acid:glycolic acid; intrinsic viscosity=0.41 dL/g corresponding to Mw ~50,000 Da) was purchased from Birmingham Polymers (Pelham, Ala.). Poly(vinyl alcohol) (PVA; 88% hydrolyzed, 25,000 Da) was obtained from Polysciences, Inc. (Warrington, Pa.). Rhodamine B base and fluorescein were obtained from Sigma (St. Louis, Mo.). Dichloromethane (DCM; HPLC grade) was obtained from Fisher Scientific (Pittsburgh, Pa.). Ethanol (Absolute—200 Proof) was obtained in house.

2. Microsphere Preparation

Uniform PLG microspheres were prepared using technology as previously described using the Precision Particle Fabrication method (Berkland C, Kim K, Pack D W. Fabrication of PLG microspheres with precisely controlled and monodisperse size distributions. J Control Release 2001 May 18; 73(1):59-74). Briefly, PLG dissolved in DCM (30% w/v) was sprayed through a small-gauge needle. The polymer stream was acoustically excited using an ultrasonic transducer (Branson Ultrasonics, Danbury, Conn.) controlled by a waveform generator (model 33220A, Agilent Technologies, Santa Clara, Calif.), resulting in regular jet instabilities that produced uniform polymer droplets. An annular carrier stream (~0.5% PVA w/v in distilled water) surrounding the droplets was produced using a nozzle coaxial to the needle. The emanated polymer/carrier streams flowed into a beaker containing approximately 1,000 mL of 0.5% PVA. To extract the solvent, incipient polymer droplets were stirred for 3-4 hours. Subsequently, the hardened microspheres were filtered and rinsed with distilled water (~1 L) to remove residual PVA. Finally, microspheres were lyophilized (Freezone, Labconco benchtop model) for 2 days and stored at −20° C. under desiccant. In a similar manner, fluorescent dye-loaded microspheres were prepared for concentration profile assessment (discussed herein) by using PLG solution (~30% w/v in DCM) co-dissolved with rhodamine B or fluorescein.

The microspheres having a uniform diameter were characterized for their size and morphology. Four sets of microparticles were produced; a) blank—220 µm, b) blank—160 µm, c) rhodamine B-loaded (10% w/w)—150 µm, and d) fluorescein-loaded (10% w/w)—150 µm. Uniform solid PLG microspheres of 220 µm diameter were used to form scaffolds for sub-studies, except the scaffolds used in scanning electron microscopic imaging (160 µm set) and flow profile assessment study (dye-loaded microspheres were also used).

3. Particle Size Distribution

The size distribution of microsphere preparations was determined using a Coulter Multisizer 3 (Beckman Coulter Inc., Fullerton, Calif.) equipped with a 560-µm aperture. Freeze-dried particles were suspended in Isoton electrolyte that was stirred at low speeds to prevent particles from settling. A minimum of 5,000 microspheres was analyzed for each set of particles.

Figure 3A:
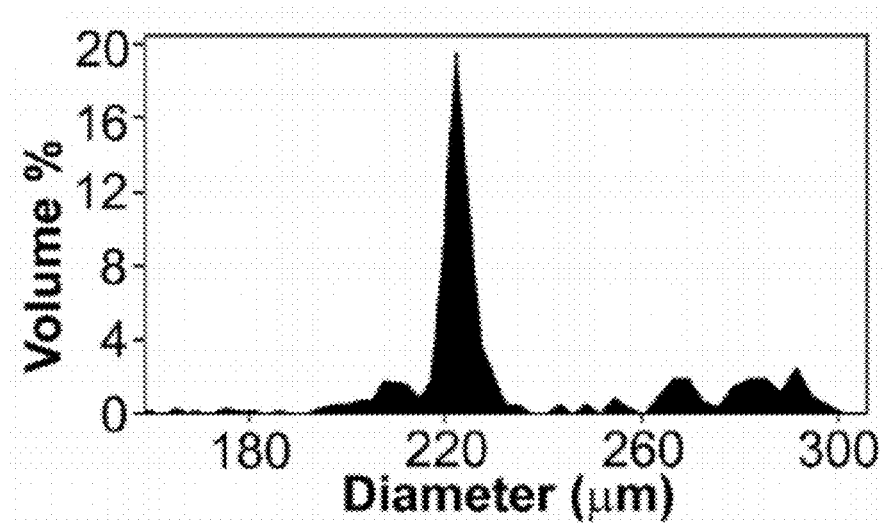
FIG. 3A is a graphical representation of the size of microspheres used in preparing a microsphere-based scaffold.
Figure 3B:
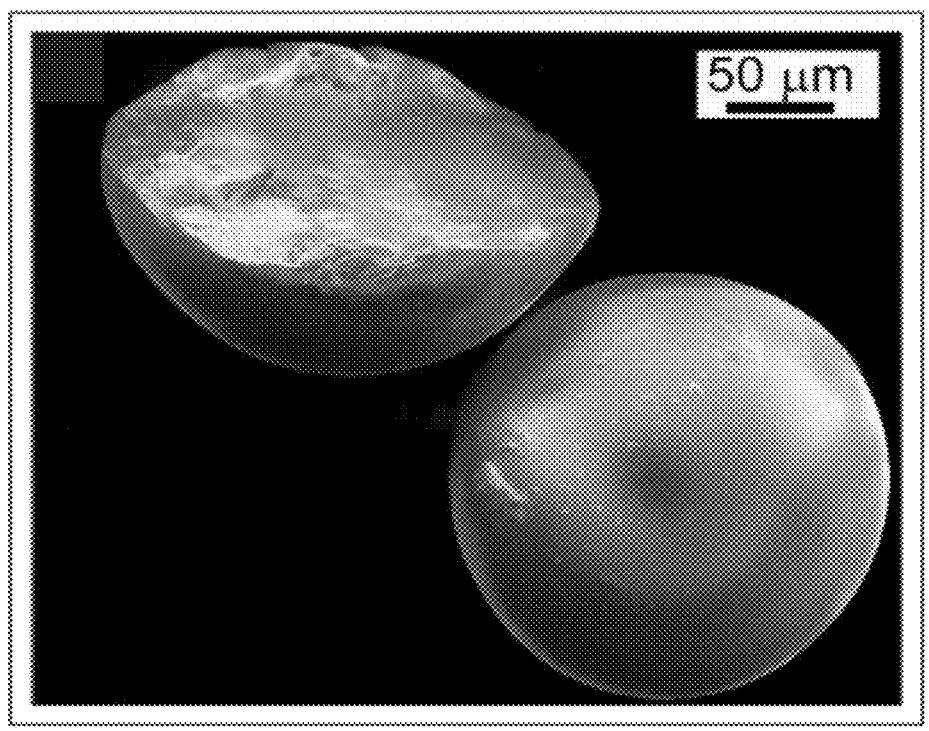
FIG. 3B is a scanning electron micrograph of external and internal structures of microspheres used in preparing a microsphere-based scaffold.

Characteristic size distribution of the microspheres revealed their relative monodispersity by the coulter multisizer size analysis distribution plot of PLGA microspheres, which shows monodispersity at a discrete peak at 220 um (FIG. 3A). In addition, scanning electron microscopic examination of the microspheres confirmed their solid interior morphology by showing the interior and exterior morphology of cryofractured microspheres (FIG. 3B).

4. Scaffold Fabrication

Two sets of freeze-dried microspheres were separately loaded into two syringes in the form of suspensions, prepared by suspending microspheres (~1% w/v) in distilled water/PVA solution (volume ratio PVA:distilled water 1:20 (PVA 0.5% w/v)). The syringes were then installed in the scaffold fabrication apparatus (FIG. 1). The suspensions were pumped through the attached tubing to a cylindrical glass mold (6 mm diameter) in a controlled manner using programmable syringe pumps (PHD 22/2000, Harvard Apparatus, Inc., Holliston, Mass.). Through the bottom of the mold, the distilled water/PVA solution was filtered, while the microparticles stacked in the mold. The suspensions in the syringes were constantly stirred magnetically to keep them homogeneous. To prevent microspheres from rapid settling or sticking to the walls of the mold, a constant level of distilled water was maintained in the mold, controlled by an additional infusion syringe pump (Harvard Apparatus, Inc.) and a vacuum pump. The stacked microspheres were washed with distilled water (~100 mL) and then were allowed to soak in ethanol (100%) for 50±20 minutes. Ethanol-soak resulted in physical fusion of adjacent microspheres, resulting in the formation of a melded matrix. The molds (containing the scaffolds) were freeze-dried (Freezone, Labconco benchtop model, Kansas City, Mo.) for a minimum of 2 days, and then the scaffolds were retrieved from the molds. In some cases, the scaffolds were prepared using suspension(s) of dye-loaded microspheres with predefined distinct flow profiles, which were later used in concentration profile assessment studies.

Melded microsphere matrices were constructed using blank microspheres of 160 µm or 220 µm diameter with 50 minutes ethanol soak-time ($S_{160-50}$ group and $S_{220-50}$, respectively). A few additional scaffolds were prepared using microspheres of 220 µm diameter and varied ethanol soak times (50±20 min). The ethanol soak-time was selected based on preliminary scaffold fabrication results, which indicated that a minimum of 30 minutes ethanol-soak was required to produce mechanically integrated scaffolds, while exceeding soaking time of 70 minutes resulted in reduced porosities. In general, the optimum range of ethanol soak-time was a function of the polymer properties (co-polymer ratio, molecular weight, etc.). Microspheres composed of PLG with lower molecular weights are expected to require shorter ethanol soak-times or dilution of ethanol for production of mechanically integrated porous matrices.

Cylindrical scaffolds, 6 mm in diameter and 4 to 9 mm in height, were prepared and their morphology was analyzed (FIGS. 4A-4D). Scanning electron micrographs of a representative scaffold from the $S_{160-50}$ group revealed that the scaffolds were porous, having interconnected pores. In addition, the effect of ethanol-soak on the microspheres was visualized, confirming that exposure to ethanol resulted in slight melting of the surface of microspheres that led to the formation of a well-connected matrix.

Changing the ethanol soak time resulted in the slight variation in the overall morphology of the scaffold. While it may be expected that an increase in ethanol soak-time would result in an increased stiffness and reduced porosity of the scaffolds, no such trends were seen in the range of ethanol-soak times examined. However, visual inspection of the scaffolds did reveal that scaffolds prepared by a 30 minutes soak did not have well-integrated microspheres, and microspheres were falling off of the ends of the scaffolds.

5. Scanning Electron Microscopy

Scanning electron microscopy was used to image the interior and surface morphology of the microspheres. A drop of distilled water containing suspended microspheres was placed directly onto an aluminum stub, which was freeze-dried overnight (Freezone, Labconco benchtop model, Kansas City, Mo.). The microspheres were frozen in liquid nitrogen, cryofractured with a razor blade, then sputter coated with gold before imaging using a Leo 1550 field emission scanning electron microscope at an accelerating voltage of 5 kV under a high vacuum.

To observe size, distribution and interconnectivity of the pores of the scaffolds, a dry scaffold was fractured with a razor blade and placed on an aluminum stub. The sample was sputter coated with gold and imaged using a Leo 1550 field emission scanning electron microscope at an accelerating voltage of 5 kV under a high vacuum.

Figure 4A:
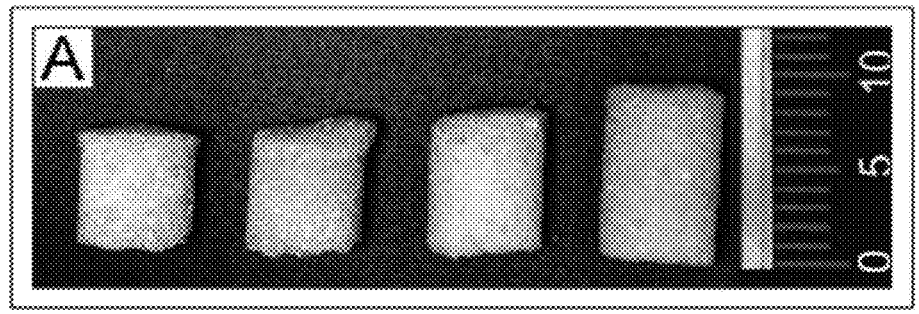
FIG. 4A is a photograph of a microsphere-based scaffold.
Figure 4B:
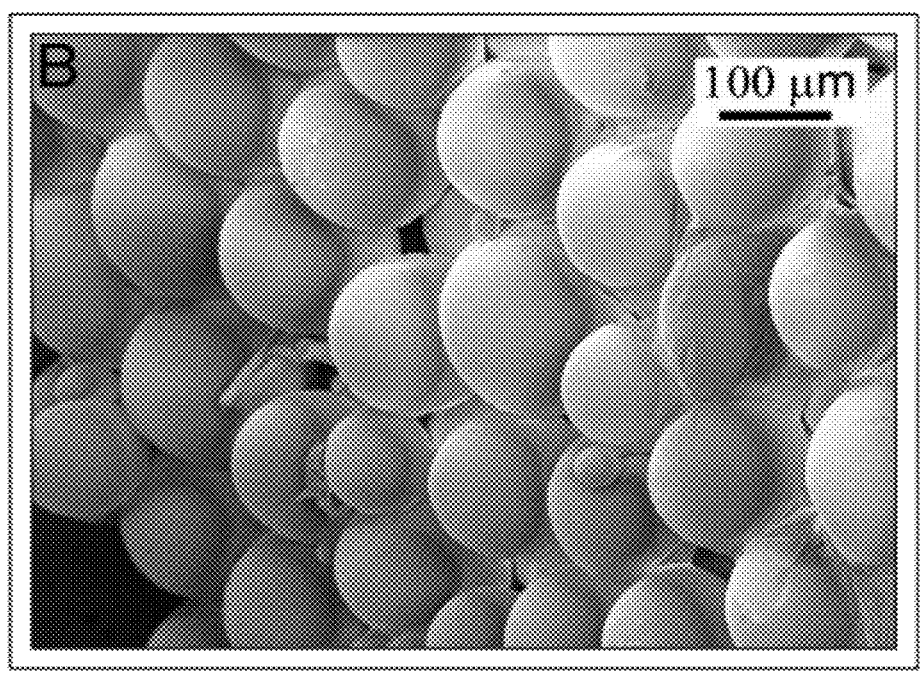
FIGS. 4B-4D are scanning electron micrographs of the microspheres and melding of microspheres of a microsphere-based scaffold.
Figure 4C:
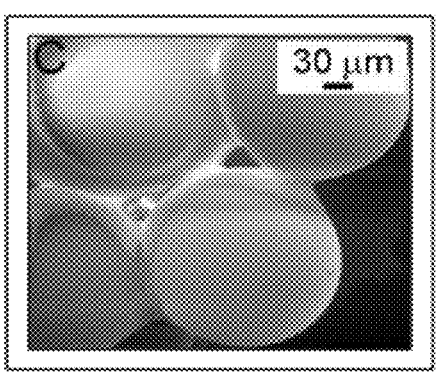
Figure 4D:
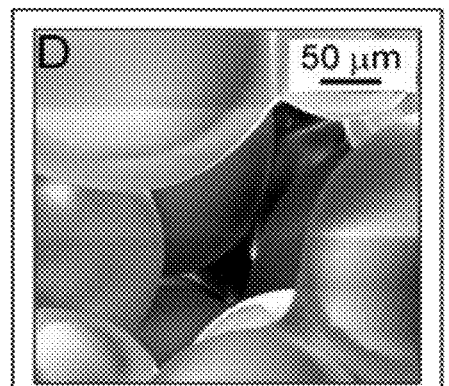

FIG. 4A shows that the scaffolds can be prepared to have the shape of the mold, which was cylindrical. The scaffold was prepared with blank microspheres of 220 um diameter with a 50 minute ethanol soak time. As such, any shape of mold can be used to prepare the scaffolds of microspheres. FIGS. 4B-4D are scanning electron micrographs of a scaffold prepared with blank microspheres of 160 um diameter. FIG. 4B illustrates the outside appearance of the scaffold and shows melding of adjacent microspheres. FIG. 4C illustrates a magnified view of the melded microspheres obtained by the ethanol soaking FIG. 4D illustrates the pores that are formed in the scaffold during the melding process.

6. Differential Scanning Calorimetry

Differential scanning calorimetry (DSC) (Q100, TA Instruments, Inc., New Castle, Del.) was used to measure the change in glass transition temperature ($T_g$) of the PLG following the microparticle and scaffold preparations. Prior to the analysis, raw PLG and one set of microspheres were lyophilized for 1 day, and a scaffold (prepared by ethanol-soak of 50 min) was lyophilized for 2 days. The experiments were carried out in triplicate on the samples (~15-20 mg each) packed in sealed aluminum pans. For each sample, a nonisothermal scan was performed from −10° C. to +80° C. at a heating rate of 10° C. min$^{-1}$ under nitrogen atmosphere, and the corresponding $T_g$ was recorded.

The effect of microsphere preparation and scaffold fabrication on the glass transition temperature of PLG was analyzed by differential scanning calorimetry. The results are reported in Table 1. Microsphere preparation led to a small drop (~1.4%) in the glass transition temperature of the raw polymer ($p<0.05$). However, the microsphere melding process resulted in reduced glass transition temperature of the PLG, where the average glass transition temperature dropped by 14% compared to raw PLG ($p<0.05$).

TABLE 1

Comparison of Glass Transition Temperatures using Differential Scanning Calorimetry[a]

| | Glass Transition Temperature (° C.) |
|---|---|
| Pure PLGA 50:50 | 41.62 ± 0.37 |
| Microspheres | 41.04 ± 0.17 |
| Scaffold[b] | 35.68 ± 0.30 |

7. Porosity Estimation

Theoretical porosities of the scaffolds were calculated using the density of the raw PLG and the apparent densities of the scaffolds prepared by 50±20 minutes ethanol-soak. The diameter (d), thickness (h) and mass (m) of the cylindrical scaffolds were measured, and porosities were calculated as:

$$\text{Porosity} = (1 - \rho_{app}/\rho) \times 100\%;$$

where $\rho_{app}$ is the apparent density of the scaffold, given by $$\rho_{app} = 4m/\pi d^2 h,$$

and ρ is the density of the raw PLG (1.34 g/mL according to the manufacturer). The mean theoretical porosities of the scaffolds prepared by 30, 50 and 70 minutes ethanol-soak were found to range between 44.9 to 49%.

8. Mechanical Characterization

Unconfined compression tests were performed using a uniaxial testing apparatus (Instron Model 5848, Canton, Mass.) with a 10 N load cell. A custom-made stainless steel bath and compression-plate assembly was mounted in the apparatus. Cylindrical scaffold samples prepared by ethanol-soak of 50±20 minutes (5 to 9 mm in height) were tested at a strain rate of 10 mm/minute at room temperature, and moduli of elasticity were obtained from the linear regions of the stress-strain curves. The stress was defined as the ratio of the load to the initial cross-sectional area, and the strain was defined as the ratio of the change in the length to the original length. The mechanical integrity of the scaffolds, analyzed by unconfined compression testing, indicated that average moduli of elasticity of these scaffolds ranged from 4.2 to 6.0 MPa (n=4).

9. Porcine Ankle Chondrocytes Isolation/Culture

Porcine chondrocytes were harvested from a hog ankle (Duroc, 6 months old, female) obtained from a local slaughterhouse. Briefly, pieces of articular cartilage were retrieved aseptically, and then minced with a scalpel. Subsequently, chondrocytes were isolated from the tissue by digestion in 30 mL of 2 mg/mL sterile collagenase (type 2, 305 U/mg; Worthington Biochemical, Lakewood, N.J.) at 37° C. overnight. The cells were then plated for expansion in monolayer and incubated at 37° C. in 5% $CO_2$, with media changed every 2-3 days. The cell culture medium consisted of Dulbecco's Modified Eagle medium, 10% Fetal bovine serum (ES cell quantified), 1% Penicillin-streptomycin-fungizone, 1% non-essential amino acids (all from Invitrogen Life Technologies, Carlsbad, Calif.) and 50 μg/mL L-ascorbic acid (tissue culture grade; Fisher Scientific, Pittsburgh, Pa.). The cells were expanded and passaged twice before being seeded onto the scaffolds.

10. Cell Seeding and Viability

Cylindrical scaffolds (~6 mm diameter) were prepared using a 50 minute ethanol soak, as mentioned earlier, and shortened with a razor blade to a height of approximately 1 mm. Cells were seeded onto these scaffolds at a density of 3×106 cells per scaffold using the orbital shaker method as described previously (Almarza A J, Athanasiou K A. Seeding techniques and scaffolding choice for tissue engineering of the temporomandibular joint disk. Tissue Eng 2004 November-December; 10(11-12):1787-1795.), and cultured for 18 days. Briefly, the scaffolds were sterilized in ethylene oxide for 12 hours and aired for one day. The scaffolds were then placed in the individual wells of a 12-well untreated plate, pre-coated with 600 μL of 2% agarose to prevent cell attachment to the wells, and incubated overnight at 37° C. in 1 mL of medium. Subsequently, the scaffolds were wetted in sterile-filtered ethanol, washed twice with PBS and once with the medium, before a highly concentrated equivalent volume of cells was dripped directly onto the middle of each scaffold. Cells were then allowed to attach to the scaffold for 2-3 hours at 37° C. After adding an additional 1 mL of medium, the well plate was allowed to stir for two days on the lowest settings in an orbital shaker at 60 rpm, and then allowed to sit for 16 days with half of the media refreshed every other day. Following this incubation period, the scaffolds were stained with LIVE/DEAD reagent (dye concentration 2 mM calcein AM, 4 mM ethidium homodimer-1; Molecular Probes, Carlsbad, Calif.) and incubated for 45 minutes, before being subjected to fluorescence microscopy (Olympus/Intelligent Innovations Spinning Disk Confocal Microscope with epifluorescence attachment).

Figure 5A:
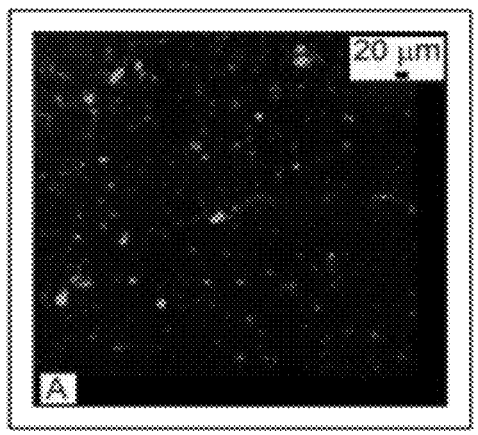
FIGS. 5A-5C are pictures of cells within a microsphere-based scaffold, where
Figure 5B:
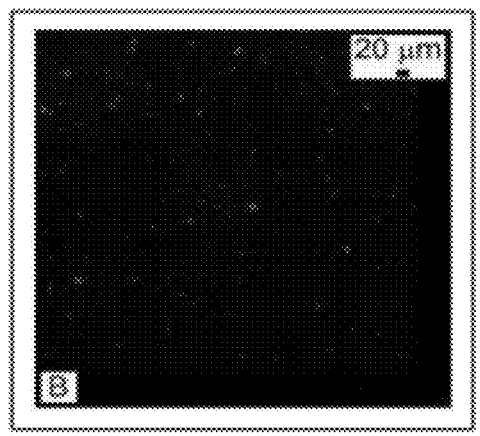
Figure 5C:
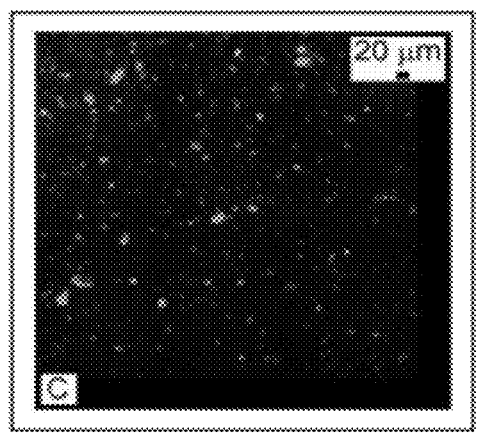
Figure 6A:
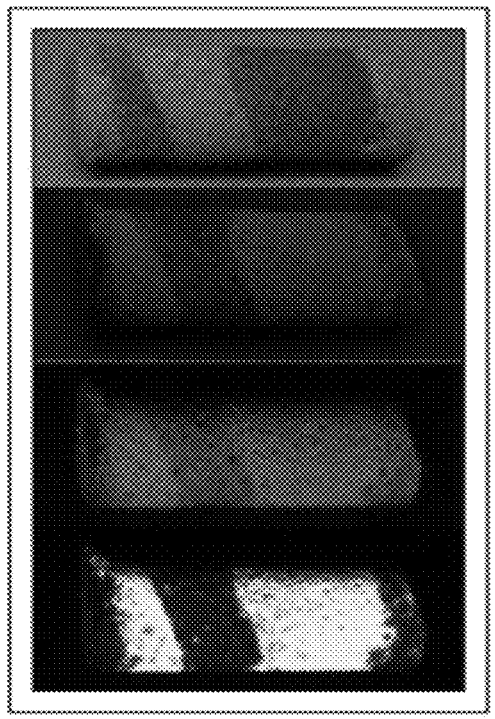
FIGS. 6A-6D are pictures of microsphere-based scaffolds having microsphere distribution properties with more than one type of microsphere.
Figure 6B:
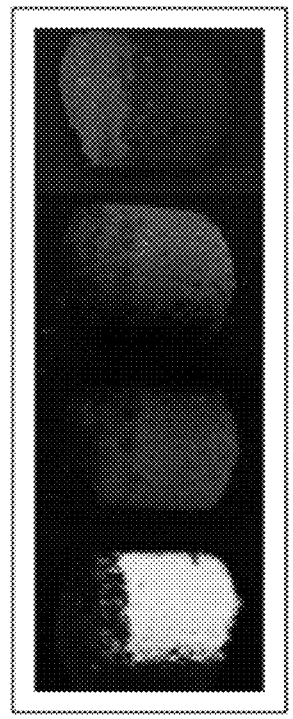
Figure 6C:
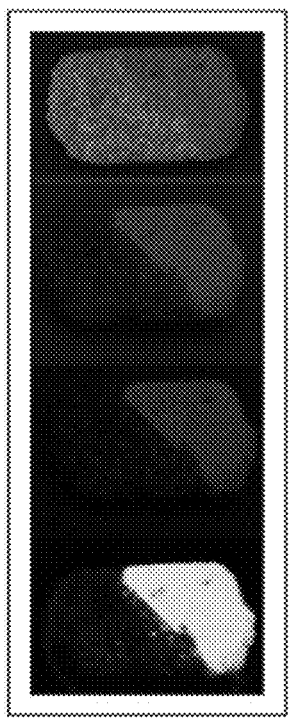
Figure 6D:
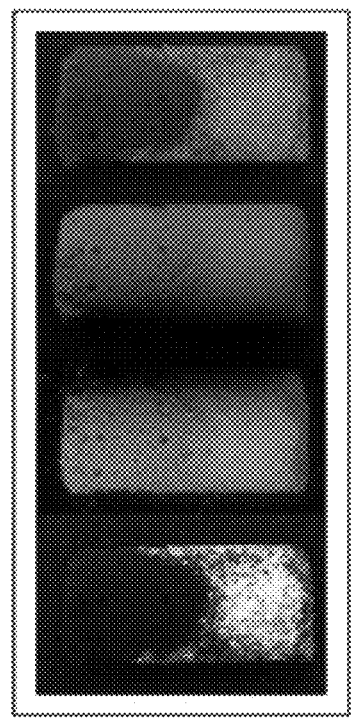
Figure 6E:
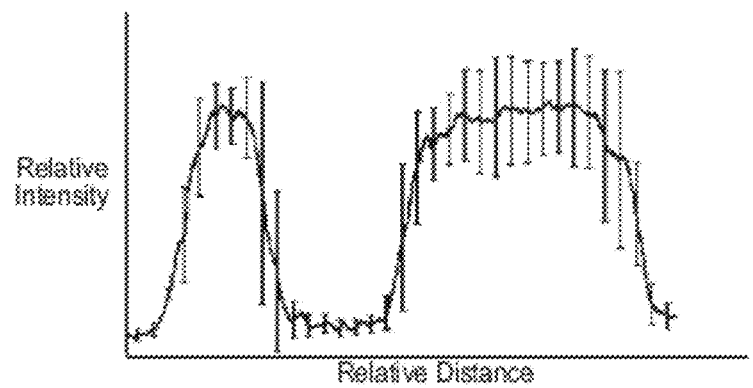
FIGS. 6E-6H are the relative intensities associated with the microspheres of FIGS. 6A-6D.
Figure 6F:
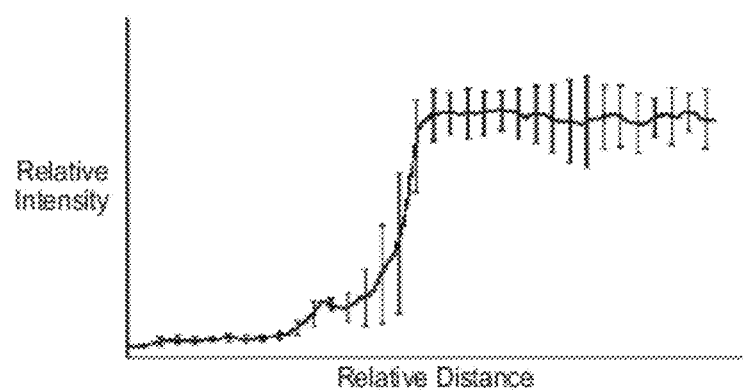
Figure 6G:
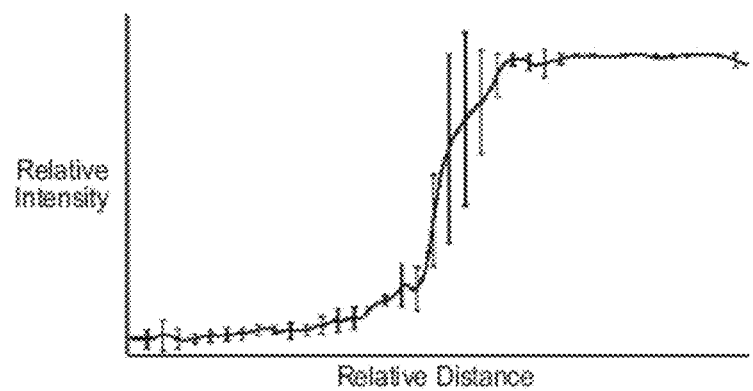
Figure 6H:
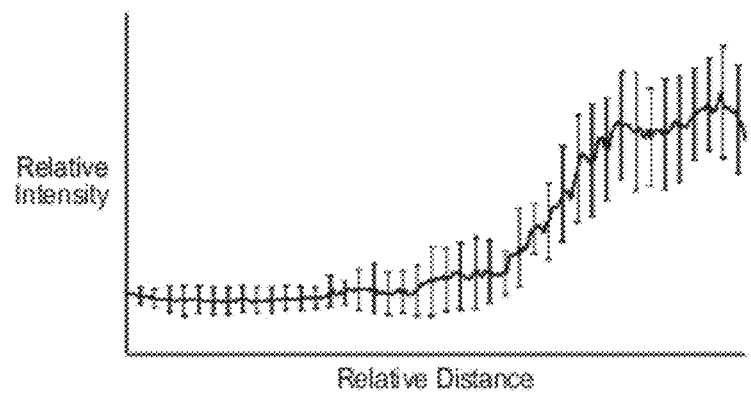

Porcine ankle chondrocytes, dynamically seeded and cultured on $S_{220-50}$ group scaffolds, were assessed for their viability. The majority of the cell population was identified as viable after a total of 18 days in culture. FIG. 5 demonstrates the results of the live/dead assay, displaying the images from a randomly selected field of view. Based on semi-automatically conducted cell counts using ImageJ software, the viability of cells was approximately 74±7% (n=3). However, as shown in FIGS. 5A-5C, some areas of dark green spots were also observed that probably were indicative of clusters of live cells. FIG. 5A shows live cells, FIG. 5B, shows dead cells, and FIG. 5C shows live and dead cells, which correlate with the cells of FIGS. 5A and 5B. The ratio of the areas stained green (FIGS. 5A and 5C, which show up as lighter spots in grayscale photos) and red (FIG. 5B-5C, which show up as lighter spots) was also calculated from the images using ImageJ software, which still led to a similar prediction of approximately 75±11% cell viability (n=3).

11. Concentration Profile Assessment Study

Figure 2A:
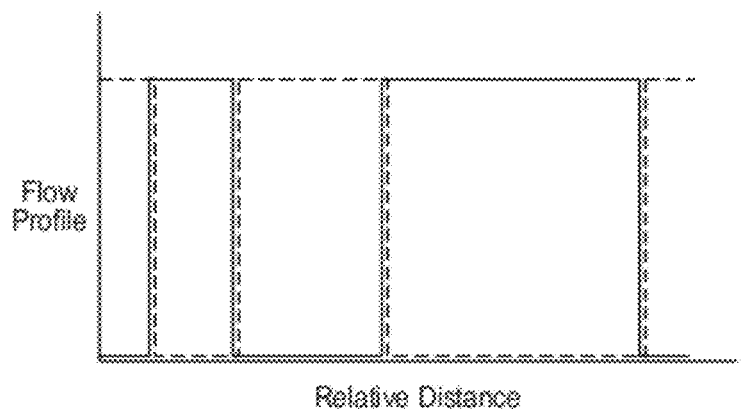
FIGS. 2A-2D are schematic representations of flow profiles of microspheres in forming a microsphere-based scaffold and can represent a microsphere gradient within a microsphere-based scaffold.
Figure 2B:
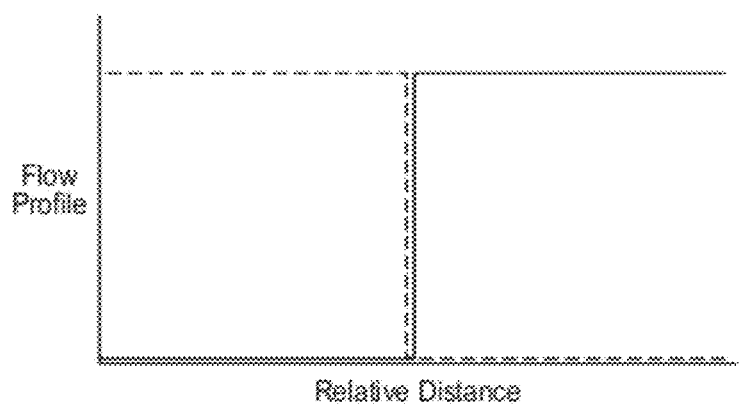
Figure 2C:
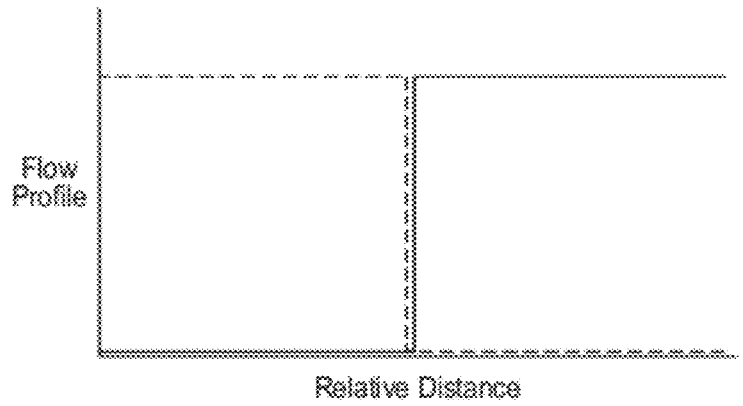
Figure 2D:
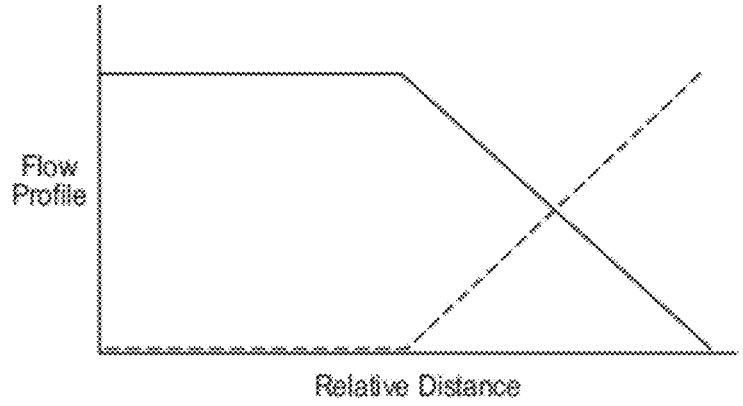

Studies were conducted to determine spatial control over composition of the scaffold. Four specific scaffolds were prepared, as mentioned earlier, using two different microsphere types (rhodamine-loaded and fluorescein-loaded microspheres, or rhodamine-loaded and blank microspheres). The syringes were loaded individually with one microsphere type and attached to the scaffold fabrication apparatus. Microspheres were pumped in a predefined manner using specific flow profiles (FIGS. 2A-2C), and then the scaffolds were prepared by melding microspheres together with an ethanol-soak of 50 minutes. Specific flow profiles were programmed into the two syringe pumps. The solid lines in the graphs of FIGS. 2A-2D illustrate the flow profile of RhodamineB-loaded microspheres with solid lines, and the dashed lines represent the flow profile of fluorescein-loaded microspheres (FIGS. 2A-2C) or blank microspheres (FIG. 2D). The resulting scaffolds were imaged under UV light using a UV lamp (254/365 nm; UVGL-25, UVP, Inc.) and a high-resolution camera (Sony Cybershot DSC-F828 8.0 MP), and images were analyzed using NIH ImageJ software to assess spatial control over the composition of the scaffolds.

Images of scaffolds that were prepared using specific flow profiles with dye-loaded or blank microsphere suspensions (described in FIGS. 2A-2D) are shown in FIGS. 6A-6D. Images of the scaffolds captured under UV light were modified by pseudo-coloring them to create black and white images. Each image was divided in five equal parts, and particle distribution in the direction perpendicular to the interface was analyzed using ImageJ software to create relative intensity vs. relative distance plots. The plots demonstrate successful fabrication of bi-layered, multi-layered and gradient scaffolds (FIGS. 6E-6H). Irrespective of the scaffolds, standard deviations were higher at the interface, probably due to imprecise settling of the microspheres in the mold and/or wetting effects on the walls of the mold. The characteristic nature of each plot, however, was similar to the corresponding flow profile applied during the scaffold fabrication. The plots demonstrate the ability of the scaffold fabrication set-up to create scaffolds of various predefined profiles with spatial control. In addition, the orientation of the interface may also be varied (compare FIGS. 6B and 6C), which can be controlled by manipulating the vertical orientation of the cylindrical mold. Note that similar flow profiles were used to prepare these two scaffolds (FIGS. 2B and 2C), the only difference being the pitch of the mold.

FIGS. 6A-6D show the loading and concentration profiles of bi layered, multilayered, and gradient scaffolds using rhodamine B loaded microspheres and fluorescein loaded or blank microspheres. The top row of FIGS. 6A-6D show that the rhodamine B loaded microspheres (darker bands; red in color) were transitioned into fluorescein-loaded (lighter bands; orange in color, FIGS. 6A-6C) or blank microspheres (lighter; white in color, FIG. 6D). The middle rows of FIGS. 6A-6D show the scaffolds under UV light (365/254 nm), and show a characteristic change in appearance of fluorescein-loaded microspheres from the lighter color to a darker color, which was blue. The bottom row of FIGS. 6A-6D shows dark pixels (red in color) from the other images that were pseudo colored in white against a black background, and were analyzed using ImageJ software to the create relative intensity versus relative distance plots of FIGS. 6E-6H (corresponding to FIGS. 6A-6D, respectively).

12. Statistical Analyses

The effect of microparticle preparation and ethanol-soak on the glass transition temperature of PLG were statistically analyzed using a three-level single factor analysis of variance (ANOVA) and a Fisher's Protected Least Significant Difference post hoc test.

13. Sub-Critical Carbon Dioxide ($CO_2$) Melding

The microsphere-based scaffold can be prepared with a sub-critical carbon dioxide ($CO_2$) technique. Sub-critical $CO_2$ is not toxic and can be used in place of organic solvents. Accordingly, poly(lactic-co-glycolic acid) microspheres of three different sizes (e.g., 100 um, 175, um, and 500 um) can be prepared. The microsphere-based scaffolds can be prepared by melding the microspheres together in a high pressure chamber at sub-critical pressures of $CO_2$. For example, sub-critical pressures can be 165 psi, 190 psi, and 220 psi, or any range therebetween. However, higher pressures can be used for larger microspheres, and lower pressures for smaller microspheres. Scanning electron micrographs of fractures of scaffolds displayed the porous nature of scaffolds and confirmed the successful melding of microspheres. Scaffolds were tested under compression in PBS at 37° C., and displayed an increase in stiffness with decreasing microsphere size. Human umbilical cord mesenchymal stromal cells (UC-MSCs) were seeded and cultured with the scaffolds. Live/Dead cell assays, histology, immunohistochemistry, and quantitative biosynthesis assays were performed, and the results demonstrated that the sub-critical carbon dioxide ($CO_2$) melding technique can be used in tissue engineering, such as in bone or cartilage tissue engineering. Also, the use of moderate carbon dioxide ($CO_2$) melding can be used to encapsulate cells during the process of scaffold fabrication in order to preserve cell viability.

Figure 9A:
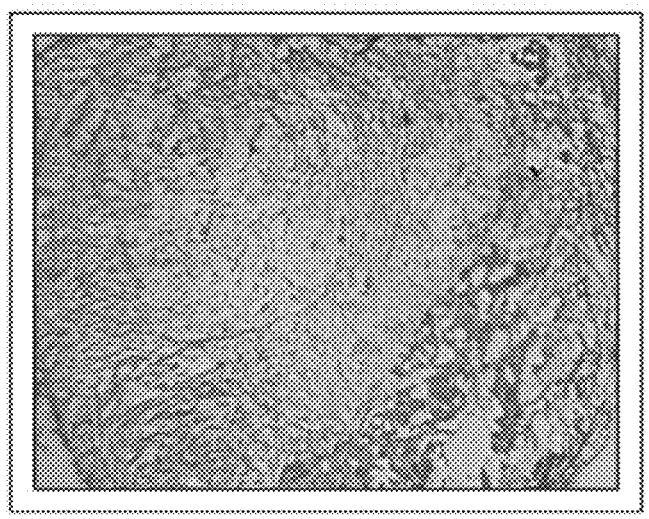
FIGS. 9A-9C are histological photographs of hUCMSCs cells from microsphere-based scaffolds as follows.
Figure 9B:
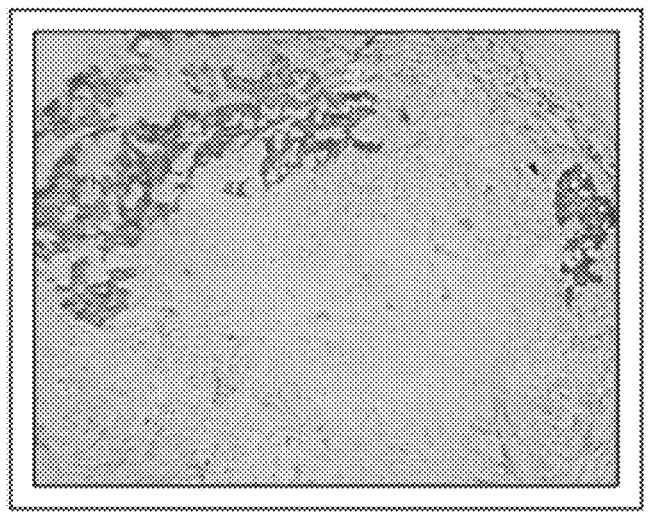
Figure 9C:
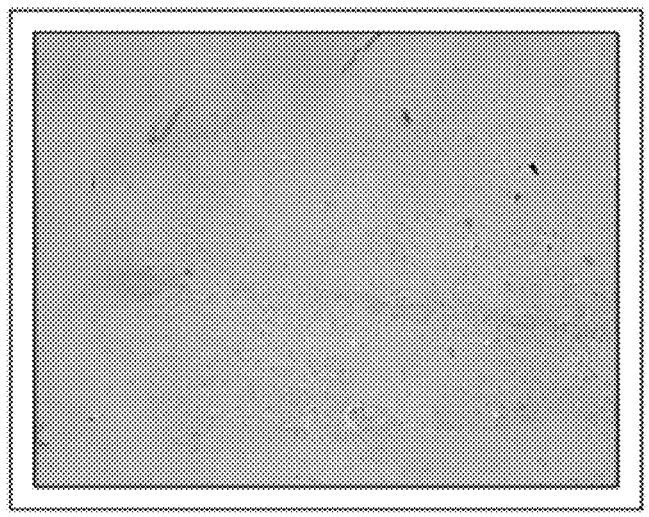
Figure 10:
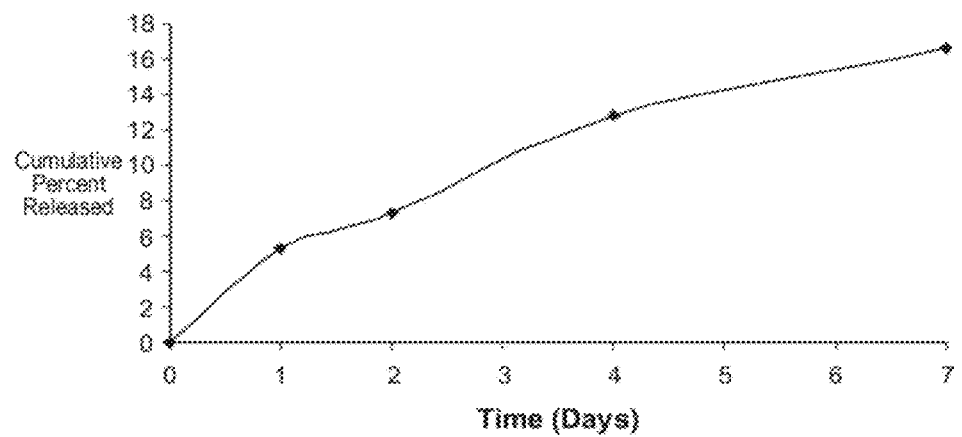
FIG. 10 is a graph of a substance release profile from a microsphere-based scaffold.

14. Cell Attachment and Matrix Synthesis hUCMSCs were cultured on the microsphere-based scaffolds for 6 weeks global with 0.1 μM dexamethasone and 10 ng/mL TGF-$\beta_1$, and produced both collagen I and II (FIGS. 9A-9C). Additionally, rUCMSCs were seeded on the scaffolds to demonstrate that we were indeed able to harvest and seed them in the scaffolds (FIG. 10). The cells of FIGS. 9A-9C were obtained after hUCMSCs were seeded on microsphere-based scaffolds for 6 weeks in chondrogenic medium and produced the following: FIG. 9A) collagen I, FIG. 9B) collagen II; and FIG. 9C) is a negative control.

15. Activity of Released Protein

The tertiary structure of a common protein (lysozyme) was evaluated by fluorescence spectroscopy before and after encapsulation in PLGA microparticles by dissolving in dimethyl sulfoxide (DMSO) and obtaining a spectrum from 310-400 nm. The peak position remained the same, with the exact peak position determined to be 339 nm for both samples (data not shown), indicating that the native structure of lysozyme was retained upon extraction from the microspheres.

16. Growth Factor Release Profile and Activity

ELISA was used to determine the entrapment efficiency and percent cumulative release of TGF-$\beta_1$ from the particles. The entrapment efficiency of TGF-$\beta_1$ was found to be 64.3%. To determine the release, 20 mg of 150 μm particles with entrapped TGF-$\beta_1$ were placed in 1 mL of PBS (20 rpm, 37° C.). At days 1, 2, 4 and 7, the entire supernatant was collected and buffer refreshed to determine the cumulative release up to 7 days (FIG. 10). Controlled release can be obtained by altering desired parameters. FIG. 10 is a graph that shows the percent cumulative release of TGF-$\beta_1$ from PLGA up to 7 days.

17. Microcomputed Tomography (μCT) Imaging

Figure 11A:
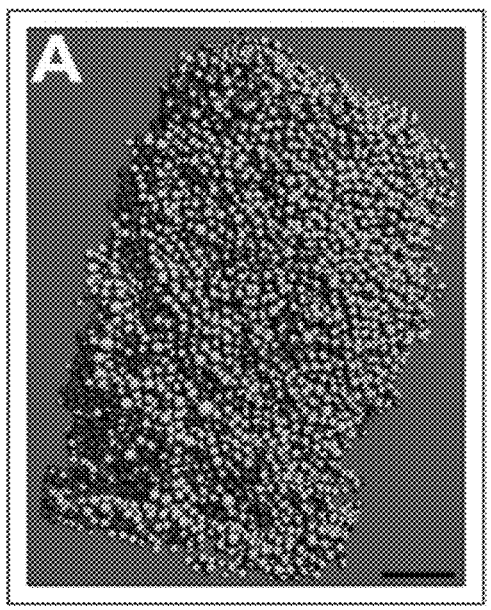
FIGS. 11A-11C are pictures of the microsphere distribution and structure within a microsphere-based scaffold obtained by microcomputed tomography (μCT) imaging.
Figure 11B:
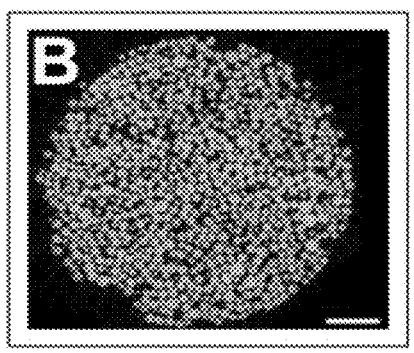
Figure 11C:
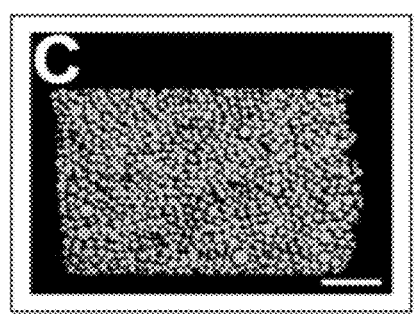

Porosity measurements for four scaffolds were performed by imaging the scaffolds with μCT (μCT 40, Scanco Medical). Using 3D reconstruction and an optimized segmentation value of 75, porosities (41.1±2.1%) and degrees of anisotropy (values were ~1.0 for homogeneous scaffolds, i.e., isotropic) were directly determined (FIG. 11A-11C). FIG. 11A-11C are μCT images, with FIG. 11A displaying the 3-D view of a scaffold, FIG. 11B displaying an image generated from the top view, and FIG. 11C displaying an image generated from a side view. The scaffolds were analyzed using ImageJ for porosity measurement. The overall porosity (n=4) was calculated to be about 41.1% (scale bars=1 mm).

18. Nanophase CaCO$_3$ Preparation

Nanophase CaCO3 can be prepared using a double water-in-oil emulsion technique. Briefly, two water-in-oil emulsions (A and B) can be prepared separately. In a typical procedure, the aqueous phase for emulsion A can include 0.1 M sodium carbonate, 0.2 M sodium hydroxide and 0.18 M sodium nitrate dissolved in 500 mL DI water. The aqueous phase for emulsion B can contain about 0.1 M calcium nitrate dissolved in 500 mL DI water. Oil phases for both the emulsions can be prepared by mixing 9.3 mL of Bis(2-ethylhexyl) hydrogen phosphate and 26.25 mL of sorbitan sesquioleate (Span-83) in 500 mL of kerosene. Water and oil phases for each emulsion can be mixed and sonicated at 50% amplitude for 2 minutes. Emulsions A and B can then be mixed together and stirred magnetically at 300 rpm for 30 minutes, allowing the reaction to occur. Following the reaction step, the system can be demulsified by adding 15% (w/w) ethylene glycol to the emulsion mixture. The settled CaCO3 particles can be washed with ethanol and water, successively, then sonicated at 15% amplitude for 1 minute before collection. The collected particles can then be freeze-dried for two days before being applied in the osteogenic microsphere preparation. A Beckman Coulter Multisizer III can measure the particle size and size distribution. The described method enables control over nanosphere size, with diameters ranging from ~200-900 nm, where particle size increases with increasing calcium ion concentration (~0.1 M to 0.25 M).

19. Fourier Transform Infrared (FTIR) Imaging

Figure 12:
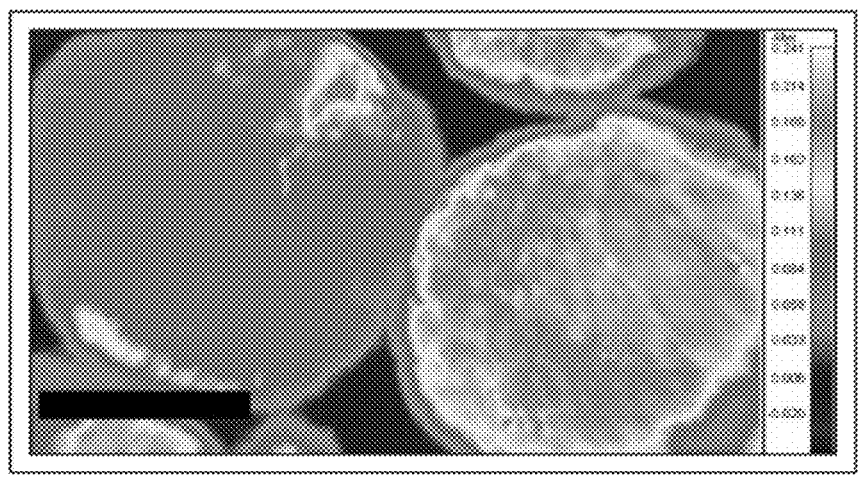
FIG. 12 is a micrograph of a microsphere having nanophase CaCO3 encapsulated (right) and a microsphere with minimal nanophase CaCO3 encapsulation (left).

Microspheres for scaffolds, some with nanophase CaCO3 encapsulated, were imaged with FTIR (Perkin-Elmer Spotlight 400, with Spectrum 400 spectrometer; ATR mode; scan parameters: 4000~750 cm-1, spectral resolution 8 cm-1, 8 scans per pixel; spatial resolution ~10 μm). The ATR spectral image using the intensity of 873 cm-1 band (□2-CO3) was used to identify the relative intensity of CaCO3 in the microsphere, as shown in FIG. 12. FTIR was able to clearly demonstrate the relative amount and distribution of CaCO3 in the microspheres, where microspheres with white portions have high levels of encapsulated CaCO3 In FIG. 12, the FTIR image is of 2 microspheres, with high CaCO3 (e.g., right microsphere sphere) and low CaCO3 (e.g., left microsphere) levels (scale bar=100 μm).

20. Mechanical Integrity of Scaffolds

Figure 13:
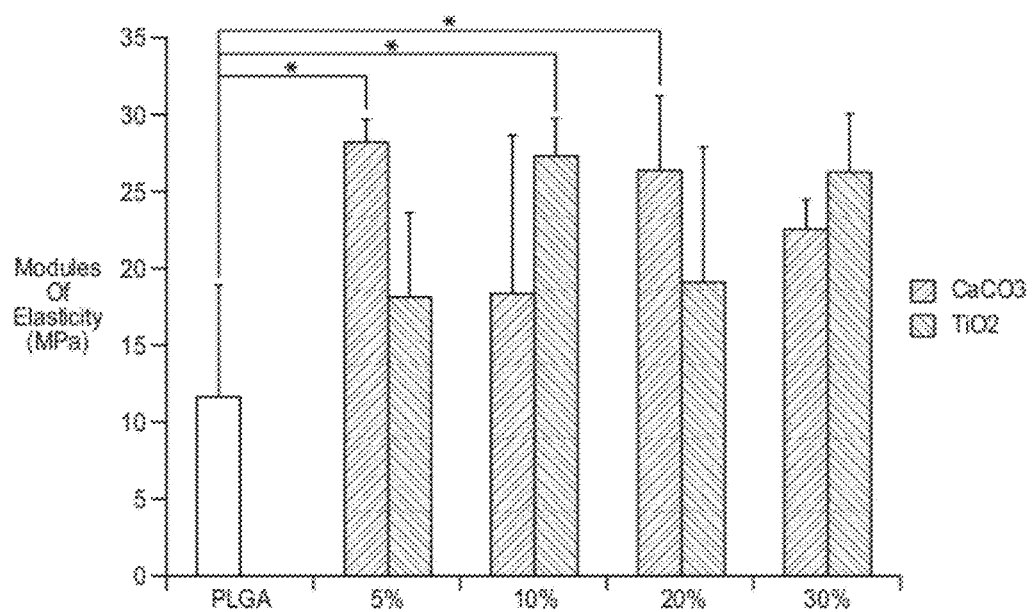
FIG. 13 is a graph illustrating the modulus of elasticity of nanophase CaCO3 microspheres and nanophase TiO2 microspheres at increasing concentrations.

Homogeneous scaffolds of either PLGA, PLGA/CaCO3, or PLGA/TiO2 microspheres were fabricated, and instantaneous moduli were determined under compression (FIG. 13). The graph in FIG. 13 illustrates the compressive moduli of PLGA, PLGA/CaCO3, and PLGA/TiO2 microsphere-based scaffolds (high strain). Composite scaffolds were markedly stiffer (e.g., the 5% CaCO3 group was 2.4 times stiffer than the pure PLGA group), which conclusively demonstrates that the nanophase materials result in a drastic increase in macroscopic mechanical integrity. This macroscopic result is comparable to AFM data, which demonstrated a 2-8 fold increase in the stiffness of PLGA microspheres with nanophase CaCO3 encapsulated.

Figure 14:
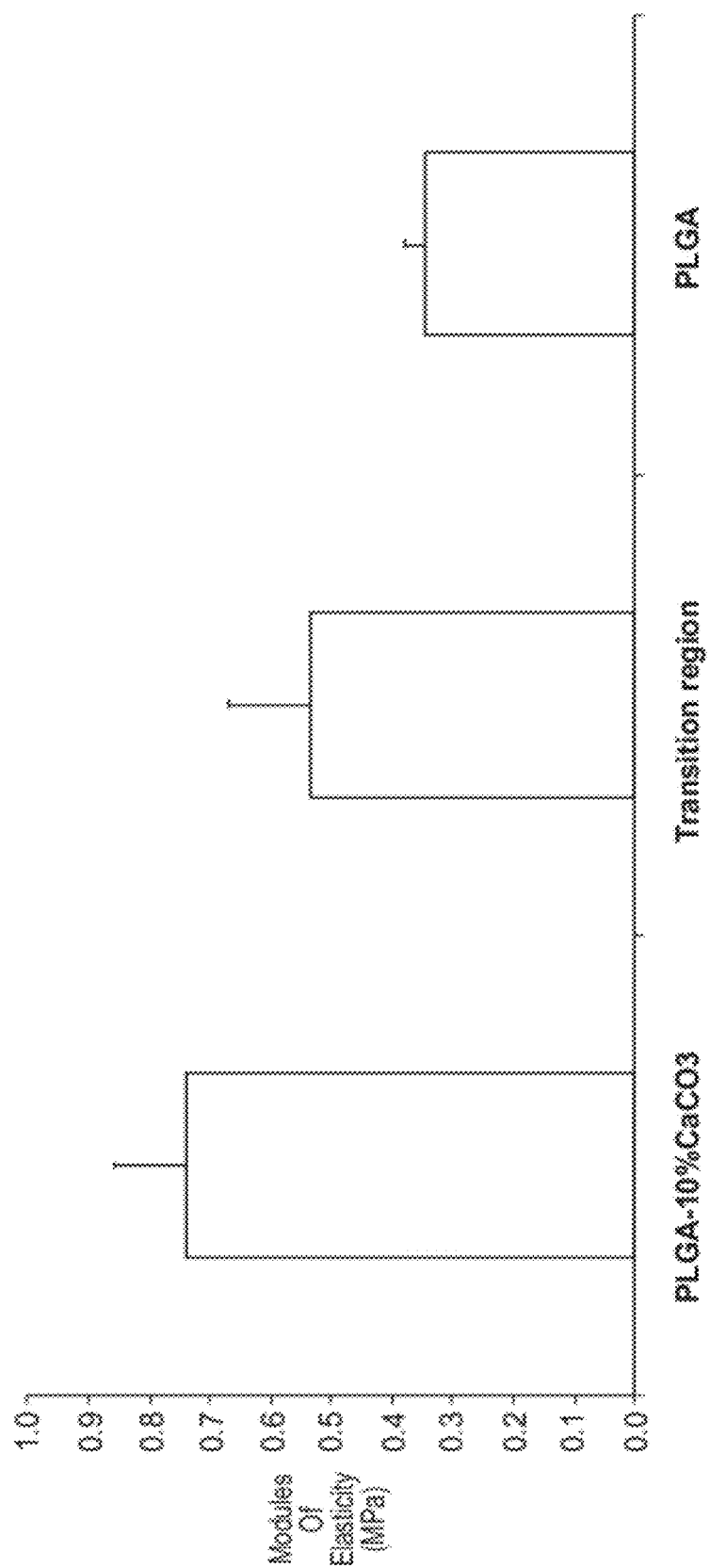
FIG. 14 is a graph illustrating the modulus of elasticity of a PLGA microsphere-based scaffold with 10% nanophase CaCO3 compared to a PLGA microsphere-based scaffold.

To further illustrate this stiffness gradient, exaggerated-length scaffolds (15 mm thick) were fabricated with opposing gradients of PLGA and PLGA/CaCO3 microspheres, and cut into thirds to demonstrate the drop in the average modulus of each section (FIG. 14). The graph in FIG. 14 illustrates macroscopic stiffness from three different regions of gradient scaffolds (lower strain). The composite end was 2.1 times stiffer than the pure PLGA end (p<0.001). Absolute magnitudes of stiffness vary between FIGS. 13 and 14 due to different strain levels, caused by microsphere compaction.

21. Microspheres Encapsulating Growth Factors

Growth factors can be tagged with a fluorescent dye in a routine manner to later monitor the maintenance of biological signal gradients of the growth factor. To conjugate dye molecules to the proteins, 10 μg of reconstituted growth factor can be mixed with 1 mL sterile PBS. Sulforhodamine B acid chloride (red color, 0.09 mg) can be mixed with dimethyl formamide (2 μL), added to the protein solution and incubated for 2 hours at 37° C. The reaction can be stopped by adding 1.5 M hydroxylamine, followed by centrifugation at 3000 g in ultracentrifugation columns for 1 hour to remove the unbound dye. A similar procedure can be followed for green fluorescent labeling with FITC dye. Uniform chondrogenic microparticles exhibiting the desired size (200 μm) can be fabricated using PLGA as a material according to techniques previously reported. An appropriate PLGA formulation (50:50 lactic acid:glycolic acid, Mw 25,000) was selected for a targeted release of 6 weeks. A typical experiment to fabricate the chondrogenic PLGA microspheres can emulsify 250 µL of a 50 mg/mL solution of reconstituted protein (TGF-β1 or TGF-β3) in deionized water into 500 mg of PLGA dissolved in 5 mL of dichloromethane. The emulsion can be formed by pulsed ultrasonication of the PLGA/protein mixture on ice at moderate power for 1 minute, a method confirmed to efficiently maintain protein structure. This emulsion can then be sprayed through a nozzle (~250 µm in diameter) that vibrates at a frequency tuned to match the jet flow-rate and the desired PLGA/protein drop size. The emerging PLGA/protein droplets can be surrounded by an additional stream of 0.5% w/v polyvinyl alcohol solution. Extraction of the dichloromethane into the continuous aqueous phase can result in the formation of solidified PLGA particles entrapping the protein. Previous experiments have verified that negligible damage occurs to proteins as a result of shear forces occurring in the nozzle apparatus (data not shown). The particles can then be collected by centrifugation and lyophilized to remove residual dichloromethane. Similar procedures can be performed for osteogenic microparticle preparation, using either PLGA or PLGA/CaCO3 (95:5 PLGA:CaCO3 w/w), and replacing the chondrogenic growth factor with BMP-2 or other biological factor. Following the preparation of microspheres, a Beckman Coulter Multisizer III can measure the particle size and size distribution. Scanning electron micrographs (LEO 1550) of selected samples offer supportive evidence of particle size and internal morphology.

22. Fabrication of Stacked Microsphere-Based Scaffolds

Heterogeneous scaffolds can be constructed by assembling chondrogenic and osteogenic microspheres together. One set of freeze-dried chondrogenic and osteogenic microparticles microspheres can be separately loaded into two syringes in the form of suspensions, prepared by suspending microspheres (~1% w/v) in DI water/PVA solution (volume ratio PVA:distilled water 1:20 (PVA 0.5% w/v)). The syringes can then be installed in the scaffold fabrication apparatus (FIG. 1). The suspensions in the syringes can be constantly stirred magnetically to keep them homogeneous. The suspensions can be pumped through the attached tubing to a cylindrical glass mold (3.5 mm diameter) in a controlled manner using programmable syringe pumps (PHD 22/2000, Harvard Apparatus, Inc., Holliston, Mass.) with the specific gradient profile consisting of a linear transitioning region. Microspheres can enter, settle and stack on the bottom of the mold (the density of particles is higher than water), while the accumulating DI water/PVA solution is filtered through the base of the mold. To prevent microspheres from rapid settling or sticking to the walls of the mold, a constant level of distilled water can be maintained in the mold, controlled by an additional infusion syringe pump (Harvard Apparatus, Inc.) and a vacuum pump. Similar procedures can be performed to create homogeneous microsphere matrices, with the only difference being that only one group of microspheres (either chondrogenic or osteogenic) will be flowed through the syringes. Also, other types of microspheres with any type of active agent can be used.

23. Differentiation of hUCMSCs

Umbilical cord matrix stem cell biology can be investigated and characterized in several applications of the microsphere-based scaffolds. Accordingly, immunology, neural application, and species differences (e.g., human, pig, dog, rat, etc.) of umbilical cord matrix stem cells can be studied with the microsphere-based scaffolds.

Porcine TMJ condylar cartilage cells and hUCMSCs were separately seeded onto PGA scaffolds for 6 days in spinner flasks, containing control and chondrogenic medium, respectively. After seeding, constructs were then each cultured in either control or chondrogenic medium for an additional 4 weeks. Although both groups were seeded at 5 million cells/mL, the hUCMSCs were 55% greater in number immediately after seeding and 2 times greater after 4 weeks. After 4 weeks, Saf-O/Fast green staining indicated a significant amount of GAG synthesis by hUCMSCs (FIG. 15), and immunohistochemical staining demonstrated a widespread presence of collagen I along with scattered collagen II in hUCMSC groups (data not shown). These results suggested a superiority of hUCMSCs over cartilage cells for cartilage tissue engineering. FIG. 15 show 4 weeks of chondrogenic differentiation, where the left column is safranin-O/fast green, and the right column is chondroitin-4-sulfate (C4S) immunostaining Top to bottom row are hUCMSCs in control (left) or chondrogenic (right) medium, TMJ cartilage cells in chondrogenic medium, and TMJ cartilage cells in control medium. The significantly higher intensity of staining in the hUCMSC constructs demonstrates that the hUCMSCs significantly outperform TMJ cartilage cells in GAG synthesis.

In an effort to improve collagen synthesis, higher cell densities were employed. Cells were seeded onto PGA scaffolds using an orbital shaker at 5M, 25M and 50M cells/mL. After 4 weeks, intense collagen I staining and localized areas of collagen II and aggrecan staining were observed in the high density groups (FIG. 16). Moreover, hydroxyproline assays confirmed that the 50 M group produced ~3 times more collagen (36±2 µg collagen/construct) than the 25M group (12±6 µg collagen/construct). FIG. 16 shows IHC staining for collagen types I and II and aggrecan after 4 weeks, where 25M and 50M refer to seeding densities in cells/mL, CI and CII refer to collagen I and II, respectively.

Additionally, hUCMSCs were compared to hBMSCs in vitro. P-5 cells were seeded onto PGA scaffolds using an orbital shaker, and immunohistochemical staining demonstrated a dramatic difference in the expressions of collagen I and aggrecan at week 3 between the two cell types (FIG. 17A). In addition, the hydroxyproline content for the hUCMSC-seeded group was 3 times higher by week 6 (FIG. 17B). These findings suggest that hUCMSCs may outperform hBMSCs for cartilage and osteochondral tissue engineering applications. FIG. 17A shows immunohistochemical staining for collagen type I and aggrecan after 3 weeks of culture on PGA scaffolds. FIG. 17B shows hydroxyproline content for hUCMSC and BMSCs after 3 and 6 weeks of culture, respectively.

24. Osteogenic Differentiation of hUCMSCs

The hUCMSCs were cultured in PGA scaffolds for a period of 6 weeks in osteogenic medium. Seeding densities of 5, 25 and 50 million cells/mL were compared, and it was discovered that the highest density group produced significantly more calcium per construct (FIG. 18) and per cell. FIG. 18 is a graph that shows calcium content increased over time, and was significantly higher for higher density hUCMSC constructs. Also, more intense von Kossa staining (data not shown) was observed. These results clearly demonstrate the osteogenic capacity of hUCMSCs in 3D tissue engineering, which has never before been demonstrated in the literature.

Such osteogenic capacity of hUCMSCs in 3D tissue engineering is surprising and unexpected.

25. In Vivo Evaluation

A preliminary study was performed to demonstrate the feasibility of using microsphere-based scaffolds for osteochondral defect repair. Defects (size: 3.5 mm height, 3 mm diameter) were generated in the knees of New Zealand White rabbits (male, ages 6-9 months), and PLGA microsphere-based scaffolds were surgically implanted (FIG. 19A-19B). Rabbits were sacrificed after 6 weeks, and implants were recovered for analysis. Visual inspection of the superior surface of the implant indicated a smooth cartilaginous tissue formation (FIG. 19B). The picture in FIG. 20A shows an osteochondral defect created in the rabbit knee (medial femoral defect), with the arrow showing the location of the defect. The picture in FIG. 19B shows the surface of the implant (in circle) appears to resemble a cartilaginous tissue, closely matching with the surrounding tissue.

Additionally, histological results provide evidence of regional cartilage and bone formation de novo. FIGS. 20A-D include histological data of the in vivo study after 6 weeks of implantation. FIG. 20A-20B show histological results following 6 weeks of implantation, and show Saf-O/Fast green staining of the implant/tissue. The large arrow indicates the tissue formed within the constructs. The small arrow indicates the surrounding tissue (control). FIG. 20C shows Von Kossa staining, which shows signs of mineralization in the implant. Also, FIG. 20D shows Alizarin Red staining, and also shows signs of mineralization in the implant.

26. In Vitro Cell Growth

Cells (e.g., human mesenchymal stem cells from bone marrow) were cultured on the a blank scaffold (e.g., control scaffold) and a gradient scaffold having opposing gradients of TGF-beta1 and BMP-2 for 6 wks. The scaffolds were constructed by melding the microspheres together with ethanol as the solvent. The mechanical integrity of the scaffolds at week 6 was very similar, reflected by their similar moduli of elasticity and relaxed moduli.

After 6 weeks, the total numbers of cells were identified per scaffold, which is shown in FIG. 21. FIG. 21 shows that both the blank scaffold and the gradient scaffold were suitable for cell growth, viability, and propagation as demonstrated by both scaffolds having a significant increase in cell numbers after 6 weeks. The overall cell number per construct increased by about 100% during the 6 week cell culture, and the differences were found to be statistically significant. Also, it should be noted that the gradient scaffold was shown to be a better scaffold.

Additionally, the amount of glycosaminoglycan (GAG) present in the cells after 6 weeks was determined. As shown in FIG. 22, both scaffolds were suitable for cell growth and GAG production. The GAG content per scaffold increased approximately 5-6 fold during the 6 week culture, and the GAG content per construct was found to be about 20% higher for the gradient scaffolds compared to the blank scaffolds Accordingly, the gradient scaffold had cells that produced significantly more GAG compared to the blank scaffold. Accordingly, the increase in GAG demonstrates that the gradient scaffold is superior over a blank scaffold. Thus, the use of microsphere gradients as described herein can be advantageous in cell culturing and tissue engineering applications.

Based on these results, the effects of chondrogenesis may be prominent during the 6 week cell culture, demonstrated by a significantly higher GAG content for the gradient scaffolds compared to the blank scaffold. An increasing trend in Alkaline phosphatase (ALP) activity for the gradient scaffold started at week 3, which may be indicative of the osteoblastic activity that began after an initial culture period. The decrease in the mechanical integrity of the constructs may be a consequence of microsphere degradation that led to the disappearance of the sintering sites with time, transitioning to the mechanical integrity of the neo-synthesized tissue.

27. Microsphere Size Distribution

Relatively monodisperse microspheres having uniform nominal diameters were created using a previously reported method (Berkland, C., Kim, K. & Pack, D. W. Fabrication of PLG microspheres with precisely controlled and monodisperse size distributions. *J Control Release* 73, 59-74 (2001)). These microspheres demonstrate a solid interior morphology. The nominal particle sizes were: 120 µm, 140 µm (both with an intrinsic viscosity (i.v.) of 0.37 dL/g), and 5 µm, 100 µm, 175 µm, 240 µm and 500 µm (i.v.=0.33 dL/g) (FIG. 23A).

28. Scaffold Shapes

Figure 23B:
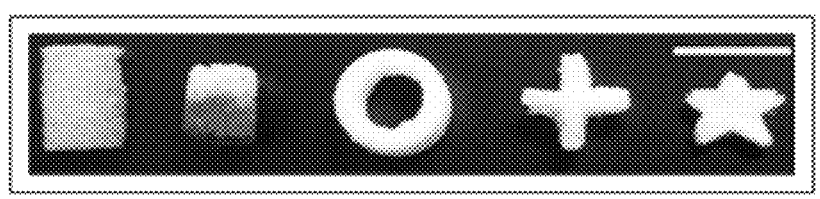

Microsphere-based cylindrical scaffolds were constructed in cylindrical plastic molds using monodisperse microspheres (~20-80 mg) of all of the sizes except for the 5 µm group. In addition, to prepare scaffolds with a bimodal population of microspheres, a mixture of two different particle types (sizes: 5 µm and 140 µm) were used. By utilizing custom rubber molds of different shapes and microspheres of size 140 µm, a variety of shape-specific scaffolds were also constructed in a similar manner (FIG. 23B). Morphological assessment of the scaffolds using scanning electron microscopy revealed that the microsphere matrices were porous, where the microspheres largely retained their shape.

29. Sub-Critical $CO_2$ Sintering

A sub-critical CO2 sintering method was used to manufacture microsphere-based scaffolds. In the past, plasticization of PLG in pressurized CO2 has been applied to create foamed scaffolds, where saturation of the polymer with CO2 was performed at sub-critical pressures (~55 bar) with equilibration periods of greater than 24 hours, and a rapid depressurization led to the nucleation of the gas (forming pores in the material) and restoration of the glass transition temperature. To prepare microsphere-based matrices in the current study, the equilibration of CO2 in the polymer was restricted by decreasing the pressure and the duration of CO2 exposure, leading to a comparatively reduced plasticized state of the PLG. While this allowed the microspheres to primarily retain their shape, the plasticization of the microsphere surfaces led to the sintering of the adjoining microspheres, yielding a porous matrix (FIG. 24A-24F). The conditions of CO2 exposure are a factor for promoting the mutual-penetration and melding of microspheres, and increasing the chain mobility at the interfaces of adjoining microspheres.

The pressure (15 bar) and duration of CO2 exposure (1 hour or less) were selected to allow sintering of all the microspheres with different sizes and i.v. of PLG. Microspheres with smaller sizes may require milder conditions, such as less pressure or shorter exposure, to achieve optimal sintering. In addition, the rate of depressurization was used to modulate the basic morphology of the scaffolds. A moderate rate of depressurization (e.g., 0.14-0.21 bar/s) was found to be optimal for the production of sintered matrices. For typical CO2 sintering conditions, instantaneous depressurization (i.e., in less than 5 s; for 64 µm diameter microspheres, i.v.=0.33 dL/g) or depressurization at very slow rates (i.e., <0.07 bar/s; for 240 µm diameter microspheres, i.v.=0.33 dL/g) led to foaming of the prepared scaffolds, depending on the microsphere size and i.v. of the polymer.

Under the CO2 sintering conditions, the extent of sintering of the microspheres can be a factor of the microspheres size (compare FIGS. 24A-24B with FIGS. 24C-24D, respectively). Also, the PLG microspheres of lower i.v. (i.e., 0.33 dL/g) displayed a distortion from the spherical morphology and a higher degree of sintering (compare FIGS. 24A and 24C with FIGS. 24B and 24D, respectively). Both the size of the microsphere and the intrinsic viscosity of the polymer were found to affect the pore sizes. As can be observed in FIGS. 24A-24F, the pore sizes for the scaffolds prepared with PLG microspheres of lower i.v. had anisotropic pores with closed pores at several places. Roughly, the average pore-sizes were around 70 µm (FIGS. 24A and 24B), 50 µm (FIG. 24C) and 40 µm (FIG. 24D). Micrographs of a single microsphere (140 µm) revealed the modifications in the surface of the microspheres following the CO2 sintering, including the microsphere connection sites (FIG. 24E). The microsphere morphology, closely resembling the appearance of a microsphere in an ethanol melding method, showed the presence of a surface film of PLG containing ripples, indicating the surface plasticization of PLG. To improve the inter-microsphere connection that could improve the mechanical characteristics of the scaffolds, scaffolds were prepared using two different groups of microspheres (140 µm and 5 µm) that were mixed together in a ratio of 1:8 by weight, respectively. Additional connecting bridges between the large microspheres were formed, however, at the loss of overall scaffold porosity, with reduced pore-sizes (FIG. 24F).

30. Mechanical Strength

Mechanical characterization of the scaffolds was performed by unconfined compression under simulated physiological conditions. The hypothesized mechanism of compression for microsphere-based matrices is somewhat analogous to the compression of closed-foam cellular solids. Following an initial linear region, a non-linear pore collapse region follows. The moduli of elasticity were determined from the stress-strain plots using the end of the initial linear regions before the onset of non-linear region (e.g., extending to about 40% strain, in general), which indicate the scaffold elasticity. The average moduli of the scaffolds ranged from 71 to 196 kPa (FIG. 25), matching the moduli of native cartilaginous tissues. The stiffnesses of the scaffolds revealed a somewhat inverse relationship between average microsphere size and average mechanical modulus. Also, a higher intrinsic viscosity of the polymer also seemed to improve the mechanical characteristics, probably because of a spherical morphology and more ordered packing of the microspheres (see FIGS. 24A-24F). In addition, inclusion of smaller interstitial spheres in the pores can lead to an increase in the average mechanical modulus (e.g., compare i.v.=0.37 vs. bimodal for the 140 µm diameter microspheres) of the scaffolds.

31. Cell Cultures

Cell culture studies were performed to determine the suitability of these scaffolds for tissue engineering. Porcine chondrocytes, dynamically seeded and cultured on the scaffolds, were assessed for their viability. The majority of the cell population was identified as viable after 3 weeks in culture (FIGS. 26A-26C). Immunohistochemistry revealed positive staining for collagen types I and II following the 3 week culture (FIG. 26II). In addition, Safranin-O staining revealed signs of glycosaminoglycan (GAG) formation for both the groups (FIG. 26D). Biochemical analysis also revealed positive indications of cartilage-like matrix formation, where the presence of GAGs and collagen were detected (Table 1).

TABLE 1

Biochemical Assay results following 3 wk cell culture[a]

| Scaffold Group | Number of cells | GAG content (µg) | Hydroxyproline content (µg) |
|---|---|---|---|
| Chondrocytes | $5.8 \pm 1.0 \times 10^4$ | $12.8 \pm 7.1$ | $1.8 \pm 0.8$ |
| HUCMSCs | $5.9 \pm 1.0 \times 10^4$ | $2.8 \pm 1.0$ | $1.8 \pm 0.4$ |

[a]Mean ± S.D.: n = 4, except for cell number for the chondrocyte-seeded group with n = 3.

32. Simultaneous Sintering and Cell-Loading

To allow for homogeneous seeding of the constructs, cell loaded matrices were fabricated via a one-step CO2 sintering of microspheres with the HUCMSCs. The conditions of sintering were altered to minimize the time of exposure (e.g., 4 min or less, excluding the depressurization time), while keeping the CO2 pressure to a relatively low value (e.g., 30 bar). Interestingly, when performed in the presence of the culture medium, the sintering process resulted in a thin patch formation, where only a few microsphere layers at the top of the mold were sintered together (FIG. 27). In contrast, in the absence of the medium, a mixture of cells with the microspheres yielded completely sintered matrices. The difference between the thin patch formation (e.g., with culture medium) and full 3D scaffold formation (e.g., absence of medium) can be attributed to the thermodynamic limitation of CO2 solubility in the liquid phase (Henry's Law).

Viability assessment of the cell-loaded thin patch and the scaffolds revealed that virtually the entire cell population survived the sintering process (FIG. 27B-27C). Although CO2 at high pressures for long durations may not be cytocompatible due to known sterilization efficacy of supercritical CO2 achieved by lowering the cytoplasmic pH from the formation of carbonic acid and the shear forces of intercellular bubble formation upon depressurization, it was demonstrated that the milder conditions with milder gaseous CO2 conditions are highly conducive to cell viability. Based on the size of the microspheres, the type of PLG, and the type of cells under consideration, various sub-critical CO2 sintering conditions may exist (i.e., a number of combinations of sub-critical pressures and exposure times), which allow for the formation of cell-loaded matrices without affecting the cell viability.

33. Microspheres with Nanophase Doping

Figure 28A:
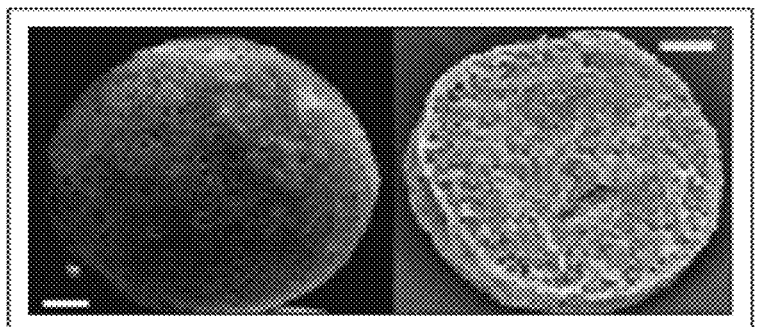
Figure 28B:
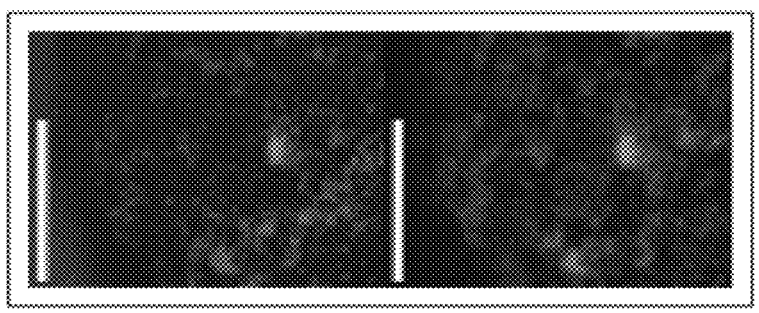
Figure 28C:
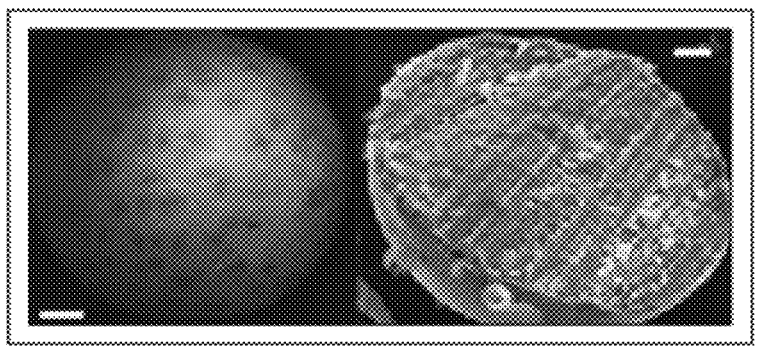
Figure 28D:
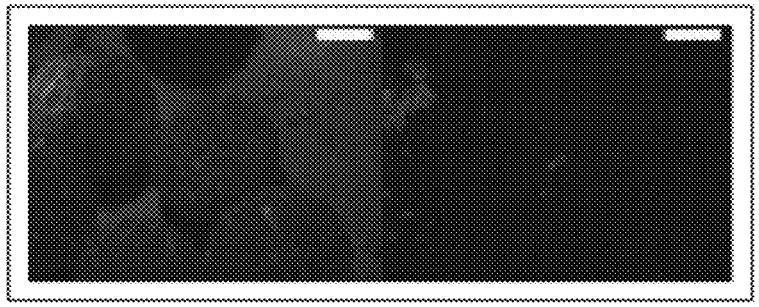

The morphological characteristics of microspheres doped with various nanophase materials were studied. Morphological analysis of microspheres was conducted using scanning electron microscopy/energy dispersive spectroscopy (SEM/EDS). FIGS. 28A and 28C display representative SEM images of intact (left) and cryofractured (right) microspheres, corresponding to 90:10 PLGA:CaCO3 and 90:10 PLGA:TiO2, respectively. FIGS. 28B and 28D show the elemental distribution of the microspheres obtained using EDS, displaying an overlay of C, O, and Ca/Ti (left) and corresponding Ca/Ti distribution (right).

FIGS. 29A-29C include characteristic SEM micrographs of a scaffold, prepared by sintering the microspheres (90:10 PLGA:CaCO3) using ethanol sintering. FIG. 29A shows the porous nature of the scaffold, and FIG. 29B shows microsphere connection sites. FIGS. 29C-29D include live/dead images of human umbilical cord mesenchymal stromal cells cultured on these scaffolds for a period of 2 weeks, demonstrating high viability. The representative images of cells in a single plain (FIG. 29C) and a 100 µm thick section (FIG. 29D) were taken from an interior section of a scaffold. This shows a significant number of live cells, which is beneficial for tissue engineering applications.

FIG. 30A is an image of a gradient scaffold prepared using dye (Rhodamine B)-loaded PLGA microspheres and 90:10 PLGA:CaCO3 microspheres using a 2 hour ethanol soak. The image was taken under UV light using a UV lamp (254/365 nm; UVGL-25, UVP, Inc.) and a high-resolution camera, and analyzed using NIH ImageJ software to plot relative intensity as a function of pixel distance. The image shows that the CaCO3 doped microspheres can be prepared in concentration gradients as described herein. FIG. 30B confirms the gradient by showing the relative distance of the microspheres from one end, by measuring the relative intensity.

FIG. 31 is a graph that shows the moduli of elasticity of the homogeneous scaffolds prepared using different types of microspheres. The moduli were obtained from the initial linear regions of the stress-train curve: 1) at 25% strain (preceding the onset of pore-collapse for PLGA scaffolds), and 2) preceding the onset of pore-collapse, in general (at 40% strain for composite scaffolds). Surface modifications that result due to the incorporation of nano-phase materials led to a decrease in the extent of sintering of the composite microspheres compared to the control PLGA microspheres for a 2 hour ethanol-soak.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references, publications, journal articles, patents, published patent applications, and the like that are disclosed herein are incorporated herein by specific reference in their entirety.

What is claimed is:

1. A method of preparing tissue engineering scaffold for growing cells, the method comprising:
    introducing a plurality of polymeric microspheres into a vessel;
    introducing $CO_2$ into the vessel;
    linking the polymeric microspheres together by a portion of each polymeric microsphere merging with a portion of at least one adjacent polymeric microsphere to form a three-dimensional matrix having a plurality of pores defined by and disposed between the polymeric microspheres, the linking being performed with the $CO_2$; and
    removing the $CO_2$.

2. A method as in claim 1, wherein the $CO_2$ is gaseous sub-critical $CO_2$.

3. A method as in claim 1, comprising introducing cells into the vessel before the linking, and wherein the linking retains cell viability.

4. A method as in claim 3, wherein the cells are introduced in an aqueous cell culture liquid that is retained during the linking.

5. A method as in claim 1, further comprising introducing a liquid into the vessel before the linking of the microspheres to provide a portion of the microspheres in contact with the liquid and a portion of the microspheres not in contact with the liquid, the liquid inhibiting linking of the polymeric microspheres in contact with the liquid in the vessel, and the portion of the microspheres in the vessel not in contact with the liquid undergoing the linking.

6. A method as in claim 5, wherein the liquid contacts an internal portion of the microspheres and inhibits linking of the internal portion of the microspheres.

7. A method as in claim 6, wherein the $CO_2$ is gaseous sub-critical $CO_2$ and only penetrates into a portion of the microspheres due to liquid inhibiting penetration of the $CO_2$.

8. A method as in claim 7, wherein the gaseous sub-critical $CO_2$ penetrates into the portion of the microspheres to form an external surface of linked microspheres.

9. A method as in claim 8, comprising removing the external surface having the linked microspheres so as to obtain a thin sheet of linked microspheres.

10. A method as in claim 1, comprising forming the three-dimensional matrix such that the plurality of polymeric microspheres have a surface area sufficient for growing cells within the plurality of pores, wherein the polymeric microspheres are dimensioned sufficiently to result in the pores between the linked polymeric microspheres.

11. A method as in claim 1, comprising forming the three-dimensional matrix such that the plurality of polymeric microspheres have:
    a first set of polymeric microspheres having a first gradient spatial distribution with a higher concentration at a first end and lower concentration at a second end of a body of the three-dimensional matrix; and
    a second set of polymeric microspheres that are different from the first set of polymeric microspheres, the second set of polymeric microspheres having a second gradient spatial distribution with a lower concentration at the first end and higher concentration at the second end of the body of the three-dimensional matrix,
    wherein the forming is by introducing the first set of microspheres into the vessel so as to have the first gradient spatial distribution and introducing the second set of microspheres into the vessel so as to have the second gradient spatial distribution.

12. A method as in claim 11, comprising the forming providing:
    a first portion at the first end being entirely polymeric microspheres of the first set; and
    a second portion at the second end being entirely polymeric microspheres of the second set.

13. A method as in claim 11, the first set of polymeric microspheres being different from the second set of polymeric microspheres in a characteristic selected from the group consisting of the following:
    type of composition; type of polymer; particle size; particle size distribution; type of bioactive agent; type of bioactive agent combination; bioactive agent concentration; amount of bioactive agent; rate of bioactive agent release from the microspheres; mechanical strength of the microspheres; flexibility of the microspheres; rigidity of the microspheres; type of cells associated with microspheres; color of the microspheres; radiotranslucency of the microspheres; or radiopaqueness of the microspheres.

14. A method as in claim 11, comprising:
    a first bioactive agent contained in or disposed on the first set of polymeric microspheres; and the second set of polymeric microspheres being substantially devoid of the first bioactive agent.

15. A method as in claim 11, comprising:
a first bioactive agent contained in or disposed on the first set of polymeric microspheres; and
a second different bioactive agent contained in or disposed on the second set of polymeric microspheres.

16. A method as in claim 11, comprising:
introducing a third set of polymeric microspheres different from the first or second set of polymeric microspheres into the vessel prior to linking.

17. A method as in claim 1, wherein the $CO_2$ is high pressure $CO_2$.

18. A method of preparing tissue engineering scaffold for growing cells, the method comprising:
introducing a first set of polymeric microspheres into a vessel;
introducing a second set of polymeric microspheres different from the first set of polymeric microspheres into the vessel;
introducing ethanol or $CO_2$ into the vessel;
linking the polymeric microspheres of the first set and second set together by a portion of each polymeric microsphere merging with a portion of at least one adjacent polymeric microsphere to form a three-dimensional matrix having a plurality of pores defined by and disposed between the polymeric microspheres, the three-dimensional matrix having:
the first set of polymeric microspheres having a first gradient spatial distribution with a higher concentration at a first end and lower concentration at a second end of body of three-dimensional matrix; and
the second set of polymeric microspheres having a second gradient spatial distribution with a lower concentration at the first end and higher concentration at the second end of the body; and
removing the ethanol or $CO_2$.

19. A method as in claim 18, comprising:
preparing a first fluid suspension of the first set of polymeric microspheres;
preparing a second fluid suspension of the second set of polymeric microspheres;
introducing the first fluid suspension into the vessel for the introduction of the first set of polymeric microspheres into the vessel; and
introducing the second fluid suspension into the vessel for the introduction of the second set of polymeric microspheres before, during, and/or after introducing the first fluid suspension into the vessel.

20. A method as in claim 18, comprising the first set of polymeric microspheres being different from the second set of polymeric microspheres in a characteristic selected from the group consisting of the following:
type of composition; type of polymer; particle size; particle size distribution; type of bioactive agent; type of bioactive agent combination; bioactive agent concentration; amount of bioactive agent; rate of bioactive agent release from the microspheres; mechanical strength of the microspheres; flexibility of the microspheres; rigidity of the microspheres; color of the microspheres; type of cells associated with microspheres; radiotranslucency of the microspheres; or radiopaqueness of the microspheres.

21. A method of preparing tissue engineering scaffold for growing cells, the method comprising:
introducing a first set of polymeric microspheres into a vessel;
introducing a second set of polymeric microspheres different from the first set of polymeric microspheres into the vessel;
introducing a medium selected from the group consisting of liquid solvent or $CO_2$ into the vessel;
linking the polymeric microspheres of the first set and second set together by a portion of each polymeric microsphere merging with a portion of at least one adjacent polymeric microsphere to form a three-dimensional matrix having a plurality of pores defined by and disposed between the polymeric microspheres, the three-dimensional matrix having:
the first set of polymeric microspheres having a first gradient spatial distribution with a higher concentration at a first end and lower concentration at a second end of a body of a three-dimensional matrix; and
the second set of polymeric microspheres having a second gradient spatial distribution with a lower concentration at the first end and higher concentration at the second end of the body; and
removing the medium.

22. A method as in claim 21, comprising:
preparing a first fluid suspension of the first set of polymeric microspheres;
preparing a second fluid suspension of the second set of polymeric microspheres;
introducing the first fluid suspension into the vessel for the introduction of the first set of polymeric microspheres into the vessel; and
introducing the second fluid suspension into the vessel for the introduction of the second set of polymeric microspheres into the vessel before, during, and/or after introducing the first fluid suspension into the vessel.

23. A method as in claim 21, comprising the first set of polymeric microspheres being different from the second set of polymeric microspheres in a characteristic selected from the group consisting of the following:
type of composition; type of polymer; particle size; particle size distribution; type of bioactive agent; type of bioactive agent combination; bioactive agent concentration; amount of bioactive agent; rate of bioactive agent release from the microspheres; mechanical strength of the microspheres; flexibility of the microspheres; rigidity of the microspheres; color of the microspheres; type of cells associated with microspheres; radiotranslucency of the microspheres; or radiopaqueness of the microspheres.

* * * * *